(12) United States Patent
Ayscough et al.

(10) Patent No.: US 7,358,265 B2
(45) Date of Patent: Apr. 15, 2008

(54) OXA- AND THIADIAZOLES AND THEIR USE AS METALLOPROTEINASE INHIBITORS

(75) Inventors: Andrew Paul Ayscough, Cambridge (GB); Stephen John Davies, Oxfordshire (GB); Gilles Pain, Bresso (IT); Jean-Yves Gillon, Collonge sous Saleve (FR)

(73) Assignees: Vernalis (R&D) Ltd, Abington, Cambridge; Laboratories Serono S.A., Aubonne (CH)

( * ) Notice: Subject to any disclaimer, the term of this patent is extended or adjusted under 35 U.S.C. 154(b) by 288 days.

(21) Appl. No.: 10/504,317

(22) PCT Filed: Feb. 20, 2003

(86) PCT No.: PCT/GB03/00741

§ 371 (c)(1),
(2), (4) Date: Apr. 27, 2005

(87) PCT Pub. No.: WO03/070711

PCT Pub. Date: Aug. 28, 2003

(65) Prior Publication Data

US 2005/0222189 A1 Oct. 6, 2005

(30) Foreign Application Priority Data

Feb. 22, 2002 (GB) ................................. 0204159.8

(51) Int. Cl.
*C07D 285/08* (2006.01)
*C07D 271/06* (2006.01)
*A61K 31/4245* (2006.01)
*A61K 31/433* (2006.01)

(52) U.S. Cl. ...................... 514/364; 514/359; 548/128; 548/131

(58) Field of Classification Search ................ 548/128, 548/131, 136, 143; 514/363, 364
See application file for complete search history.

(56) References Cited

U.S. PATENT DOCUMENTS

2001/0021718 A1  9/2001  Bailey et al.

FOREIGN PATENT DOCUMENTS

| WO | 95 23790 | 9/1995 |
| WO | 96 33176 | 10/1996 |
| WO | WO 9947529 A1 * | 9/1999 |

OTHER PUBLICATIONS

Chen, Jian Jeffery et al. "Design, Synthesis, Activity, and Structure of a Novel Class of Matrix Metalloproteinase Inhibitors Containing a Heterocyclic P2'-P3' Amide Bond Isostere", Bioorganic & Medicinal Chemistry Letters, vol. 6, No. 13, pp. 1601-1606 1996.
Vu, Chi B. et al. "Nonpeptidic SH2 Inhibitors of the Tyrosine Kinase ZAP-70", Bioorganic & Medicinal Chemistry Letters, vol. 9, pp. 3009-3014 1999.

* cited by examiner

*Primary Examiner*—Rebecca Anderson
*Assistant Examiner*—Michael P. Barker
(74) *Attorney, Agent, or Firm*—Oblon, Spivak, McClelland, Maier & Neustadt, P.C.

(57) ABSTRACT

Compounds formula (IA) or (IB), wherein W represents HO(C=O)—, HONH(C=O)— or H(C=O)N(OH)—; X represents —O— or —S—; and $R_1$, $R_2$, and $R_3$ are as defined in the description and claims, are inhibitors of matrix metalloproteinases, in particular MMP9 and/or MMP12.

33 Claims, 2 Drawing Sheets

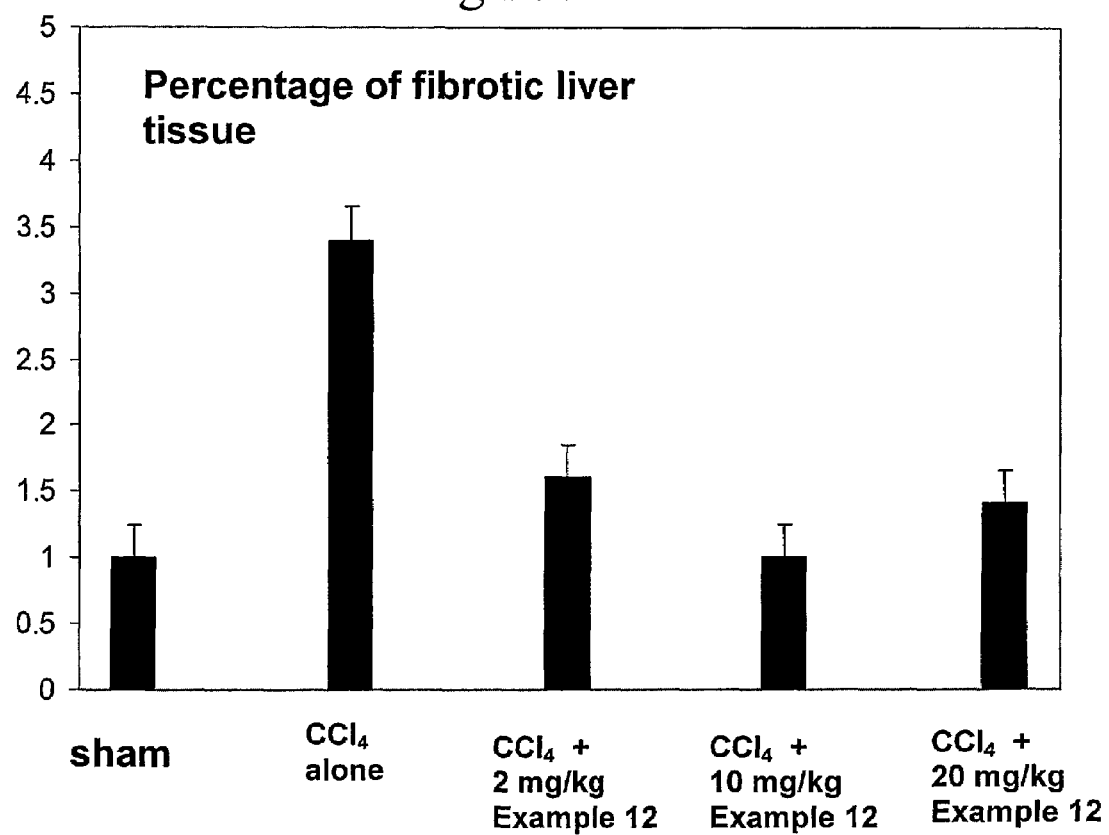

OXA- AND THIADIAZOLES AND THEIR USE AS METALLOPROTEINASE INHIBITORS

Figure 1:
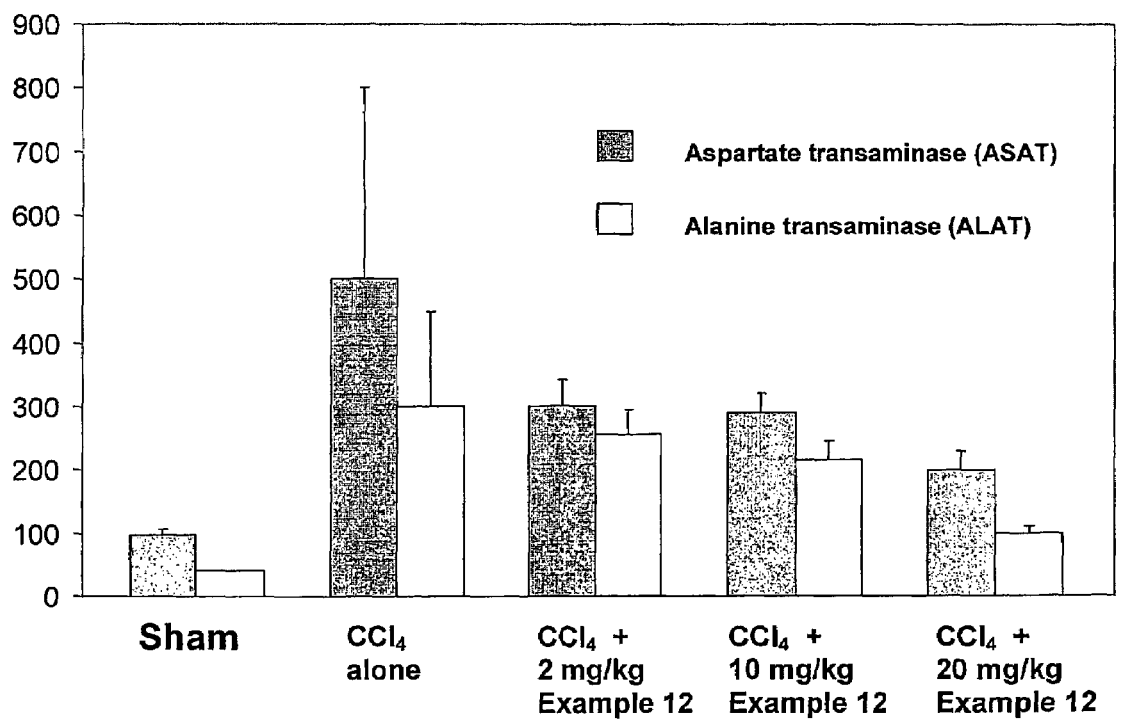

The present invention relates to therapeutically active hydroxamic and carboxylic acid derivatives, to processes for their preparation, to pharmaceutical compositions containing them, and to the use of such compounds in medicine. In particular, the compounds are inhibitors of matrix metalloproteinases.

BACKGROUND TO THE INVENTION

The matrix metalloproteinases (MMP's) are a family of zinc containing endopeptidases which are capable of cleaving large biomolecules such as the collagens, proteoglycans and gelatins. Imbalance between active MMPs and endogenous inhibitors, leads to excessive tissue disruption. The three main groups of MMPs are the collagenases, the gelatinases, and the stromelysins. Collagenases include fibroblast collagenase (MMP-1), neutrophil collagenase (MMP-8), and collagenase 3 (MMP-13). Gelatinases include 72 kDa gelatinase (gelatinase A; MMP-2) and 92 kDa gelatinase (gelatinase B; MMP-9). Stromelysins include stromelysin 1 (MMP-3), stromelysin 2 (MMP-10) and matrilysin (MMP-7). However there are MMPs which do not fit neatly into the above groups, for example metalloelastase (MMP-12), membrane-type MMP (MT-MMP or MMP-14) and stromelysin 3 (MMP-11).

Over-expression and activation of MMPs have been linked with a wide range of diseases such as cancer; rheumatoid arthritis; osteoarthritis; chronic inflammatory disorders, such as asthma, bronchitis and emphysema; cardiovascular disorders, such as atherosclerosis; corneal ulceration; dental diseases such as gingivitis and periodontal disease; neurological disorders, such as multiple sclerosis and restenosis. For example, MMP-12 is required for the development of cigarette smoke-induced emphysema in mice, Science, 277, 2002 (1997). Inhibition of MMPs is therefore a strategy for treatment of such disease states. However, there is evidence that non-selective inhibition of matrix metalloproteinase activity may affect normal physiological process leading to dose limiting side effects. Selective inhibition of MMP-12 and/or MMP-9 is thought to be a particularly relevant strategy for intervention in inflammatory conditions.

MMPs can hydrolyse the membrane-bound precursor of the pro-inflammatory cytokine tumour necrosis factor a (TNF-α). This cleavage yields mature soluble TNF-α and the inhibitors of MMPs can block production of TNF-α both in vitro and in vivo. This pharmacological action is a probable contributor to the anti-inflammatory action of this class of compounds.

For a recent review of MMP inhibition as reflected in the patent literature, see Doherty et. Al. Therapeutic Developments in Matrix Metalloproteinase Inhibition; Expert Opinions on Therapeutic Patents, 2002, 12, 665-707.

BRIEF DESCRIPTION OF THE INVENTION

The present invention provides a class of compounds which are inhibitors of MMPs. The class includes compounds which are selective inhibitors of MMP-12 relative to the collagenases and stromelysins. In addition, compounds of the invention can exhibit selective activity towards MMP-9. Compounds of the invention are therefore indicated for treatment of diseases primarily mediated by MMP-9 and/or MMP-12, especially inflammatory conditions such as multiple sclerosis and fibrosis.

DETAILED DESCRIPTION OF THE INVENTION

According to the present invention there is provided compound formula (IA or (IB))

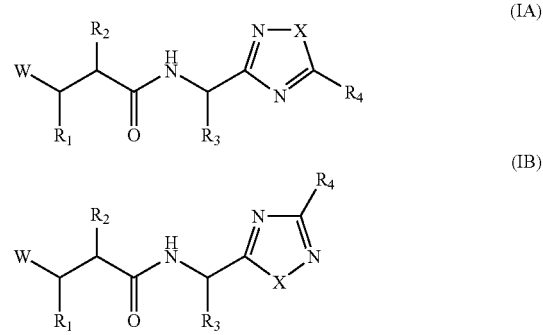

wherein
W represents HO(C=O)—, HONH(C=O)— or H(C=O)N(OH)—;
X represents —O— or —S—;
$R_1$ represents
  hydrogen;
  —OH or —SH;
  fluoro or chloro;
  —$CF_3$;
  ($C_1$-$C_6$)alkyl;
  ($C_1$-$C_6$)alkoxy;
  ($C_2$-$C_6$)alkenyl;
  phenyl or substituted phenyl;
  phenyl ($C_1$-$C_6$)alkyl or substituted phenyl($C_1$-$C_6$)alkyl;
  phenyl ($C_2$-$C_6$)alkenyl or substituted phenyl($C_2$-$C_6$)alkenyl heterocyclyl or substituted heterocyclyl;
  heterocyclyl($C_1$-$C_6$)alkyl or substituted heterocyclyl($C_1$-$C_6$)alkyl;
  a group $BSO_n$A- wherein n is 0, 1 or 2 and B is hydrogen or a ($C_1$-$C_6$)alkyl, phenyl, substituted phenyl, heterocyclyl substituted heterocyclyl, ($C_1$-$C_6$)acyl, phenacyl or substituted phenacyl group, and A represents ($C_1$-$C_6$)alkylene;
  —$NH_2$, ($C_1$-$C_6$)alkylamino or di($C_1$-$C_6$)alkylamino;
  amino($C_1$-$C_6$)alkyl, ($C_1$-$C_6$)alkylamino($C_1$-$C_6$)alkyl, di($C_1$-$C_6$)alkylamino($C_1$-$C_6$)alkyl, hydroxy($C_1$-$C_6$)alkyl, mercapto($C_1$-$C_6$)alkyl or carboxy($C_1$-$C_6$)alkyl wherein the amino-, hydroxy-, mercapto- or carboxyl-group are optionally protected or the carboxyl-group amidated; or
  a cycloalkyl, cycloalkenyl or non-aromatic heterocyclic ring containing up to 3 heteroatoms, any of which may be (i) substituted by one or more substituents selected from $C_1$-$C_6$ alkyl, $C_2$-$C_6$alkenyl, halo, cyano (—CN), —$CO_2$H, —$CO_2$R, —$CONH_2$, —CONHR, —CON(R)$_2$, —OH, —OR, oxo-, —SH, —SR, —NHCOR, and —$NHCO_2$R wherein R is $C_1$-$C_6$alkyl or benzyl and/or (ii) fused to a cycloalkyl or heterocyclic ring;
$R_2$ represents a group $R_{10}$—(X)$_n$-(ALK)$_m$- wherein
  $R_{10}$ represents hydrogen, or a $C_1$-$C_6$ alkyl, $C_2$-$C_6$ alkenyl, $C_2$-$C_6$ alkynyl, cycloalkyl, aryl, or heterocyclyl group, any of which may be unsubstituted or substituted by ($C_1$-$C_{12}$)alkyl, ($C_1$-$C_{12}$)alkoxy, hydroxy, mercapto, ($C_1$-$C_{12}$)alkylthio, amino, halo (including fluoro, chloro, bromo and iodo), trifluoromethyl, cyano, nitro, oxo, —COOH, —CONH$_2$, —COOR$^A$, —NHCOR$^A$, —CONHR$^A$, —NHR$^A$, —NR$^A$R$^B$, or CONR$^A$R$^B$ wherein R$^A$ and R$^B$ are independently a (C$_1$-C$_6$)alkyl group and ALK represents a straight or branched divalent C$_1$-C$_6$ alkylene, C$_2$-C$_6$ alkenylene, or C$_2$-C$_6$ alkynylene radical, and may be interrupted by one or more non-adjacent —NH—, —O— or —S— linkages, X represents —NH—, —O—, —S—, —NR$^C$ or —NCOR$^C$ wherein R$^C$ is a (C$_1$-C$_{12}$)alkyl group and m and n are independently 0 or 1;

R$_3$ represents the side chain of a natural or non-natural alpha amino acid;

R$_4$ represents optionally substituted
C$_1$-C$_6$ alkyl,
C$_2$-C$_6$ alkenyl,
C$_2$-C$_6$ alkynyl,
C$_1$-C$_3$ perfluoroalkyl,
cycloalkyl,
cycloalkyl(C$_1$-C$_6$ alkyl)-,
cycloalkenyl,
cycloalkenyl(C$_1$-C$_6$ alkyl)-,
phenyl,
phenyl(C$_1$-C$_6$ alkyl)-,
naphthyl,
non-aryl heterocyclyl,
non-aryl heterocyclyl(C$_1$-C$_6$ alkyl)-,
heteroaryl; or
heteroaryl(C$_1$-C$_6$ alkyl)-;

and pharmaceutically acceptable salts hydrates and solvates thereof.

As used herein the term "(C$_1$-C$_6$)alkyl" means a straight or branched chain alkyl moiety having from 1 to 6 carbon atoms, including for example, methyl, ethyl, n-propyl, iso-propyl, n-butyl, isobutyl, sec-butyl, t-butyl, n-pentyl and n-hexyl.

As used herein the term "divalent (C$_1$-C$_6$)alkylene radical" means a saturated hydrocarbon chain having from 1 to 6 carbon atoms and two unsatisfied valences.

As used herein the term "(C$_2$-C$_6$)alkenyl" means a straight or branched chain alkenyl moiety having from 2 to 6 carbon atoms having at least one double bond of either E or Z stereochemistry where applicable. The term includes, for example, vinyl, allyl, 1- and 2-butenyl and 2-methyl-2-propenyl.

As used herein the term "divalent (C$_2$-C$_6$)alkenylene radical" means a hydrocarbon chain having from 2 to 6 carbon atoms, at least one double bond, and two unsatisfied valences.

As used herein the term "C$_2$-C$_6$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent (C$_2$-C$_6$)alkynylene radical" means a hydrocarbon chain having from 2 to 6 carbon atoms, at least one triple bond, and two unsatisfied valences.

As used herein the term "cycloalkyl" means a saturated alicyclic moiety having from 3-8 carbon atoms and includes, for example, cyclopropyl, cyclobutyl, cyclopentyl, cyclohexyl, cycloheptyl and cyclooctyl.

As used herein the term "cycloalkenyl" means an unsaturated alicyclic moiety having from 3-8 carbon atoms and includes, for example, cyclopropenyl, cyclobutenyl, cyclopentenyl, cyclohexenyl, cycloheptenyl and cyclooctenyl. In the case of cycloalkenyl rings of from 5-8 carbon atoms, the ring may contain more than one double bond.

As used herein the term "aryl" refers to a mono-, bi- or tri-cyclic carbocyclic aromatic group, and to groups consisting of two covalently linked monocyclic carbocyclic aromatic groups. Illustrative of such groups are phenyl, biphenyl and napthyl.

As used herein the unqualified term "heterocyclyl" or "heterocyclic" includes "heteroaryl" as defined below, and in particular means a 5-8 membered aromatic or non-aromatic heterocyclic ring containing one or more heteroatoms selected from S, N and O, and optionally fused to a benzyl or second heterocyclic ring, and the term includes, for example, pyrrolyl, furyl, thienyl, piperidinyl, imidazolyl, oxazolyl, thiazolyl, thiadiazolyl, thiazepinyl, pyrazolyl, pyridinyl, pyrrolidinyl, pyrimidinyl, morpholinyl, piperazinyl, indolyl, and benzimidazolyl rings.

As used herein the term "heteroaryl" refers to a 5- or 6-membered aromatic ring containing one or more heteroatoms, and optionally fused to a benzyl or pyridyl ring; and to groups consisting of two covalently linked 5- or 6-membered aromatic rings each containing one or more heteroatoms; and to groups consisting of a monocyclic carbocyclic aromatic group covalently linked to a 5- or 6-membered aromatic rings containing one or more heteroatoms. Illustrative of such groups are thienyl, furyl, pyrrolyl, imidazolyl, benzimidazolyl, thiazolyl, pyrazolyl, isoxazolyl, isothiazolyl, triazolyl, thiadiazolyl, oxadiazolyl, pyridinyl, pyridazinyl, pyrimidinyl, pyrazinyl, triazinyl, 4-([1,2,3]-thiadiazoly-4-yl)phenyl and 5-isoxazol-3-ylthienyl.

As used herein the unqualified term "carbocyclyl" or "carbocyclic" refers to a 5-8 membered ring whose ring atoms are all carbon.

Unless otherwise specified in the context in which it occurs, the term "substituted" as applied to any moiety herein means substituted with up to four substituents, each of which independently may be (C$_1$-C$_6$)alkyl, phenyl, benzyl, (C$_1$-C$_6$)alkoxy, phenoxy, hydroxy, mercapto, (C$_1$-C$_6$)alkylthio, amino, halo (including fluoro, chloro, bromo and iodo), trifluoromethyl, cyano, nitro, oxo, —COOH, —CONH$_2$, —COR$^A$, —COOR$^A$, —NHCOR$^A$, —CONHR$^A$, —NHR$^A$, —NR$^A$R$^B$, or —CONR$^A$R$^B$ wherein R$^A$ and R$^B$ are independently a (C$_1$-C$_6$)alkyl group. In the case where "substituted" means substituted by benzyl, the phenyl ring thereof may itself be substituted with any of the foregoing, except phenyl or benzyl.

As used herein the terms "side chain of a natural alpha-amino acid" and "side chain of a non-natural alpha-amino acid" mean the group R$^x$ in respectively a natural and non-natural amino acid of formula NH$_2$—CH(R$^x$)—COOH.

Examples of side chains of natural alpha amino acids include those of alanine, arginine, asparagine, aspartic acid, cysteine, cystine, glutamic acid, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid, and thyroxine.

In natural alpha-amino acid side chains which contain functional substituents, for example amino, carboxyl, hydroxy, mercapto, guanidyl, imidazolyl, or indolyl groups as in arginine, lysine, glutamic acid, aspartic acid, tryptophan, histidine, serine, threonine, tyrosine, and cysteine, such functional substituents may optionally be protected.

Likewise, in the side chains of non-natural alpha amino acids which contain functional substituents, for example amino, carboxyl, hydroxy, mercapto, guanidyl, imidazolyl, or indolyl groups, such functional substituents may optionally be protected.

The term "protected" when used in relation to a functional substituent in a side chain of a natural or non-natural alpha-amino acid means a derivative of such a substituent which is substantially non-functional. The widely used handbook by T. W. Greene and P. G. Wuts "Protective Groups in Organic Synthesis" Second Edition, Wiley, N.Y., 1991 reviews the subject. For example, carboxyl groups may be esterified (for example as a $C_1$-$C_6$ alkyl ester), amino groups may be converted to amides (for example as a $NHCOC_1$-$C_6$ alkyl amide) or carbamates (for example as an $NHC(=O)OC_1$-$C_6$ alkyl or $NHC(=O)OCH_2Ph$ carbamate), hydroxyl groups may be converted to ethers (for example an $OC_1$-$C_6$ alkyl or a $O(C_1$-$C_6$ alkyl)phenyl ether) or esters (for example a $OC(=O)C_1$-$C_6$ alkyl ester) and thiol groups may be converted to thioethers (for example a tert-butyl or benzyl thioether) or thioesters (for example a $SC(=O)C_1$-$C_6$ alkyl thioester).

There are at least two actual or potential chiral centres in the compounds according to the invention because of the presence of asymmetric carbon atoms. The presence of several asymmetric carbon atoms gives rise to a number of diastereoisomers with R or S stereochemistry at each chiral centre. The invention includes all such diastereoisomers and mixtures thereof. Currently, the preferred stereo configuration of the carbon atom carrying the $R_2$ group is R; that of the carbon atom carrying the $R_1$ group (when asymmetric) is R; and that of the carbon atom carrying the $R_3$ group (when asymmetric) is S.

The Group $R_1$ $R_1$ may be, for example,
- hydrogen, hydroxy, methyl, methoxy, trifluoromethyl, ethyl, n-propyl, allyl phenylpropyl, cyclopropylmethyl, phenylprop-2-enyl, thienylsulphanylmethyl, thienylsulphinylmethyl, or thienylsulphonylmethyl; or
- $C_1$-$C_4$ alkyl, eg methyl, ethyl n-propyl or n-butyl, substituted by a phthalimido, 1,2-dimethyl-3,5-dioxo-1,2,4-triazolidin-4-yl, 3-methyl-2,5-dioxo-1-imidazolidinyl, 3,4,4-trimethyl-2,5-dioxo-1-imidazolidinyl, 2-methyl-3,5-dioxo-1,2,4-oxadiazol-4-yl, 3-methyl-2,4,5-trioxo-1-imidazolidinyl, 2,5-dioxo-3-phenyl-1-imidazolidinyl, 2-oxo-1-pyrrolidinyl, 2,5-dioxo-1-pyrrolidinyl or 2,6-dioxopiperidinyl, 5,5-dimethyl-2,4-dioxo-3-oxazolidinyl, hexahydro-1,3-dioxopyrazolo[1,2,a][1,2,4]-triazol-2-yl, or a naphthalimido (i.e. 1,3-dihydro-1,3-dioxo-2H-benz[f]isoindol-2-yl), 1,3-dihydro-1-oxo-2H-benz[f]isoindol-2-yl, 1,3-dihydro-1,3-dioxo-2H-pyrrolo[3,4-b]quinolin-2-yl, or 2,3-dihydro-1,3-dioxo-1H-benz[d,e]isoquinolin-2-yl group; or
- cyclohexyl, cyclooctyl, cycloheptyl, cyclopentyl, cyclobutyl, cyclopropyl, tetrahydropyranyl or morpholinyl.

Presently preferred $R_1$ groups include hydrogen, hydroxy, methoxy, cyclopentyl, n-propyl, and allyl. Of these, hydrogen, hydroxy, methoxy and allyl are presently more preferred.

The Group $R_2$ $R_2$ may for example be
- $C_1$-$C_{12}$ alkyl, $C_3$-$C_6$ alkenyl or $C_3$-$C_6$ alkynyl;
- cycloalkyl($C_1$-$C_6$ alkyl)-;
- phenyl($C_1$-$C_6$ alkyl)-, phenyl($C_3$-$C_6$ alkenyl)- or phenyl($C_3$-$C_6$ alkynyl)- optionally substituted in the phenyl ring;
- heteroaryl($C_1$-$C_6$ alkyl)-, heteroaryl($C_3$-$C_6$ alkenyl)- or heteroaryl($C_3$-$C_6$ alkynyl)- optionally substituted in the heteroaryl ring;
- 4-phenylphenyl($C_1$-$C_6$ alkyl)-, 4-phenylphenyl($C_3$-$C_6$ alkenyl)-, 4-phenylphenyl($C_3$-$C_6$ alkynyl)-, 4-heteroarylphenyl($C_1$-$C_6$ alkyl)-, 4-heteroarylphenyl($C_3$-$C_6$ alkenyl)-, 4-heteroarylphenyl($C_3$-$C_6$ alkynyl)-, optionally substituted in the terminal phenyl or heteroaryl ring;
- phenoxy($C_1$-$C_6$ alkyl)- or heteroaryloxy($C_1$-$C_6$ alkyl)- optionally substituted in the phenyl or heteroaryl ring;

Specific examples of such groups include methyl, ethyl, n- or iso-propyl, n-, iso- or tert-butyl, n-pentyl, n-hexyl, n-heptyl, n-nonyl, n-decyl, prop-2-yn-1-yl, cyclohexylethyl, cyclopentylmethyl, 3-phenylprop-2-yn-1-yl, 3-(2-chlorophenyl)prop-2-yn-1-yl, benzyl phenylpropyl, 4-chlorophenylpropyl, 4-methylphenylpropyl, 4-methoxyphenylpropyl, phenoxybutyl, 3-(4-pyridylphenyl)propyl-, 3-(4-(4-pyridyl)phenyl)prop-2-yn-1-yl, 3-(4-phenylphenyl)propyl-, 3-(4-phenyl)phenyl)prop-2-yn-1-yl and 3-[(4-chlorophenyl)phenyl]propyl-.

Presently preferred $R_2$ groups include benzyl, n-butyl, iso-butyl, n-hexyl, ethoxyphenylpropyl, preferably 4-ethoxyphenylpropy,l and cyclopentylmethyl. Of these, isobutyl and ethoxyphenylpropyl, particularly 4-ethoxyphenylpropyl, are presently more preferred.

The Group $R_3$ $R_3$ may for example be $C_1$-$C_6$ alkyl, phenyl, 2-, 3-, or 4-pyridyl, 2- or 3-thienyl, 2-, 3-, or 4-hydroxyphenyl, 2-, 3-, or 4-methoxyphenyl, 2-, 3-, or 4-pyridylmethyl, benzyl, 2-, 3-, or 4-hydroxybenzyl, 2-, 3-, or 4-benzyloxybenzyl, 2-, 3-, or 4-$C_1$-$C_6$ alkoxybenzyl, or benzyloxy($C_1$-$C_6$alkyl)-; or the characterising group of a natural α-amino acid, in which any functional group may be protected, any amino group may be acylated and any carboxyl group present may be amidated; or a group -[Alk]$_n$$R_6$ where Alk is a ($C_1$-$C_6$)alkyl or ($C_2$-$C_6$)alkenyl group optionally interrupted by one or more —O—, or —S— atoms or —N($R_7$)— groups [where $R_7$ is a hydrogen atom or a ($C_1$-$C_6$)alkyl group], n is 0 or 1, and $R_6$ is an optionally substituted cycloalkyl or cycloalkenyl group; or a benzyl group substituted in the phenyl ring by a group of formula —OCH$_2$COR$_8$ where $R_8$ is hydroxyl, amino, ($C_1$-$C_6$)alkoxy, phenyl($C_1$-$C_6$)alkoxy, ($C_1$-$C_6$) alkylamino, di(($C_1$-$C_6$)alkyl)amino, phenyl($C_1$-$C_6$) alkylamino, the residue of an amino acid or acid halide, ester or amide derivative thereof, said residue being linked via an amide bond, said amino acid being selected from glycine, □ or □ alanine, valine, leucine, isoleucine, phenylalanine, tyrosine, tryptophan, serine, threonine, cysteine, methionine, asparagine, glutamine, lysine, histidine, arginine, glutamic acid, and aspartic acid; or a heterocyclic($C_1$-$C_6$)alkyl group, either being unsubstituted or mono- or di-substituted in the heterocyclic ring with halo, nitro, carboxy, ($C_1$-$C_6$)alkoxy, cyano, ($C_1$-$C_6$)alkanoyl, trifluoromethyl ($C_1$-$C_6$)alkyl, hydroxy, formyl, amino, ($C_1$-$C_6$)alkylamino, di-($C_1$-$C_6$)alkylamino, mercapto, ($C_1$-$C_6$)alkylthio, hydroxy($C_1$-$C_6$) alkyl, mercapto($C_1$-$C_6$)alkyl or ($C_1$-$C_6$)alkylphenylmethyl; or a group —CR$_a$R$_b$R$_c$ in which:
each of R$_a$, R$_b$ and R$_c$ is independently hydrogen, ($C_1$-$C_6$)alkyl, ($C_2$-$C_6$)alkenyl, ($C_2$-$C_6$)alkynyl, phenyl($C_1$-$C_6$)alkyl, ($C_3$-$C_8$)cycloalkyl; or $R_c$ is hydrogen and $R_a$ and $R_b$ are independently phenyl or heteroaryl such as pyridyl; or $R_c$ is hydrogen, $(C_1\text{-}C_6)$alkyl, $(C_2\text{-}C_6)$alkenyl, $(C_2\text{-}C_6)$alkynyl, phenyl$(C_1\text{-}C_6)$alkyl, or $(C_3\text{-}C_8)$cycloalkyl, and $R_a$ and $R_b$ together with the carbon atom to which they are attached form a 3 to 8 membered cycloalkyl or a 5- to 6-membered heterocyclic ring; or $R_a$, $R_b$ and $R_c$ together with the carbon atom to which they are attached form a tricyclic ring (for example adamantyl); or $R_a$ and $R_b$ are each independently $(C_1\text{-}C_6)$alkyl, $(C_2\text{-}C_6)$alkenyl, $(C_2\text{-}C_6)$alkynyl, phenyl$(C_1\text{-}C_6)$alkyl, or a group as defined for $R_c$ below other than hydrogen, or $R_a$ and $R_b$ together with the carbon atom to which they are attached form a cycloalkyl or heterocyclic ring, and $R_c$ is hydrogen, —OH, —SH, halogen, —CN, —CO$_2$H, $(C_1\text{-}C_4)$perfluoroalkyl, —CH$_2$OH, —CO$_2(C_1\text{-}C_6)$alkyl, —O$(C_1\text{-}C_6)$alkyl, —O$(C_2\text{-}C_6)$alkenyl, —S$(C_1\text{-}C_6)$alkyl, —SO$(C_1\text{-}C_6)$alkyl, —SO$_2(C_1\text{-}C_6)$alkyl, —S$(C_2\text{-}C_6)$alkenyl, —SO$(C_2\text{-}C_6)$alkenyl, —SO$_2(C_2\text{-}C_6)$alkenyl or a group -Q-W wherein Q represents a bond or —O—, —S—, —SO— or —SO$_2$— and W represents a phenyl, phenylalkyl, $(C_3\text{-}C_8)$cycloalkyl, $(C_3\text{-}C_8)$cycloalkylalkyl, $(C_4\text{-}C_8)$cycloalkenyl, $(C_4\text{-}C_8)$cycloalkenylalkyl, heteroaryl or heteroarylalkyl group, which group W may optionally be substituted by one or more substituents independently selected from, hydroxyl, halogen, —CN, —CO$_2$H, —CO$_2(C_1\text{-}C_6)$alkyl, —CONH$_2$, —CONH$(C_1\text{-}C_6)$alkyl, —CONH$(C_{1\text{-}6}$alkyl$)_2$, —CHO, —CH$_2$OH, $(C_1\text{-}C_4)$perflouralkyl, —O$(C_1\text{-}C_6)$alkyl, —S$(C_1\text{-}C_6)$alkyl, —SO$(C_1\text{-}C_6)$alkyl, —SO$_2(C_1\text{-}C_6)$alkyl, —NO$_2$, —NH$_2$, —NH$(C_1\text{-}C_6)$alkyl, —N$((C_1\text{-}C_6)$alkyl$)_2$, —NHCO$(C_1\text{-}C_6)$alkyl, $(C_1\text{-}C_6)$alkyl, $(C_2\text{-}C_6)$alkenyl, $(C_2\text{-}C_6)$alkynyl, $(C_3\text{-}C_8)$cycloalkyl, $(C_4\text{-}C_8)$cycloalkenyl, phenyl or benzyl.

Examples of particular $R_3$ groups include benzyl, phenyl, cyclohexylmethyl, pyridin-3-ylmethyl, tert-butoxymethyl, iso-propyl, iso-butyl, sec-butyl, tert-butyl, 1-benzylthio-1-methylethyl, 1-methylthio-1-methylethyl, and 1-mercapto-1-methylethyl.

Presently preferred $R_3$ groups include phenyl, benzyl, tert-butoxymethyl, iso-propyl, tert-butyl, and iso-butyl. Of these, tert-butyl and benzyl are presently more preferred.

The Group $R_4$ $R_4$ may be, for example, $(C_1\text{-}C_6)$alkyl such as methyl, ethyl, n- or iso-propyl, prop-2-yl, and tert-butyl; $(C_3\text{-}C_8)$cycloalkyl such as cyclopropyl or cyclopentyl; phenyl; phenyl$(C_1\text{-}C_6$alkyl)- such as benzyl; heteroaryl$(C_1\text{-}C_6$alkyl)- such as thienylmethyl; monocyclic heterocyclic such as morpholino; or monocyclic heteroaryl such as thienyl or furanyl. Any of the foregiong may optionally be substituted, for example by methyl, trifluoromethyl, hydroxy, mercapto, amino or carboxy.

As mentioned above, the present compounds are useful in human or veterinary medicine since they are active as inhibitors of MMPs. Accordingly in another aspect, this invention concerns:

(i) a method of management (by which is meant treatment or prophylaxis) of diseases or conditions mediated by MMPs in mammals, in particular in humans, which method comprises administering to the mammal an effective amount of a compound which is a member of the group defined above, or a pharmaceutically acceptable salt thereof; and (ii) a compound which is a member of the group defined above, for use in human or veterinary medicine, particularly in the management (by which is meant treatment or prophylaxis) of diseases or conditions mediated by MMP; and (iii) the use of a compound which is a member of the group defined above in the preparation of an agent for the management (by which is meant treatment or prophylaxis) of diseases or conditions mediated by MMPs.

Diseases or conditions mediated by MMPs include those involving tissue breakdown such as bone resorption, inflammatory diseases, dermatological conditions and tumour growth or invasion by secondary metastases; in particular rheumatoid arthritis, osteoarthritis, periodontitis, gingivitis, corneal ulceration, neuroinflammatory disorders, including those involving myelin degradation, for example multiple sclerosis; restenosis, emphysemia, brochitis and asthma.

In a further aspect of the invention there is provided a pharmaceutical or veterinary composition comprising a compound which is a member of the group defined above together with a pharmaceutically or veterinarily acceptable excipient or carrier.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy. Optimum dose levels and frequency of dosing will be determined by clinical trial.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

Compounds according to the present invention in which W is a hydroxamic acid group HONH(C=O)— may be prepared from corresponding compounds of the invention in which W is a carboxyl group —COOH or from the corresponding protected hydroxamic acid derivatives. That process, which forms another aspect of the invention, comprises causing an acid of general formula (IIA) or (IIB)

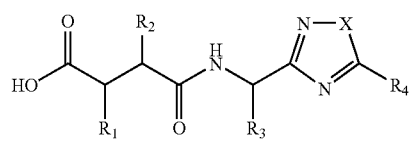

(IIA)

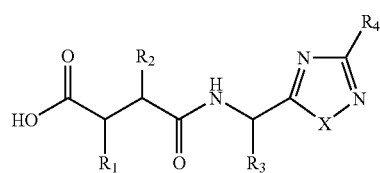

(IIB)

or an activated derivative thereof to react with hydroxylamine, O-protected hydroxylamine, or an N,O-diprotected hydroxylamine, or a salt thereof, X, $R_1$, $R_2$, $R_3$, and $R_4$ being as defined in general formula (IA) or (IB) except that any substituents in $R_1$, $R_2$, $R_3$, and $R_4$ which are potentially reactive with hydroxylamine, O-protected hydroxylamine, the N,O-diprotected hydroxylamine or their salts may themselves be protected from such reaction, then removing any protecting groups from the resultant hydroxamic acid moiety and from any protected substituents in $R_1$, $R_2$, $R_3$, and $R_4$.

Conversion of (IIA) or (IIB) to an activated derivative such as the pentafluorophenyl, hydroxysuccinyl, or hydroxybenzotriazolyl ester may be effected by reaction with the appropriate alcohol in the presence of a dehydrating agent such as dicyclohexyl dicarbodiimide (DCC), N,N-dimethylaminopropyl-N-ethyl carbodiimide (EDC), or 2-ethoxy-1-ethoxycarbonyl-1,2-dihydroquinoline (EEDQ).

Protecting groups as referred to above are well known per se, for example from the techniques of peptide chemistry. Amino groups are often protectable by benzyloxycarbonyl, t-butoxycarbonyl or acetyl groups, or in the form of a phthalimido group. Hydroxy groups are often protectable as readily cleavable ethers such as the t-butyl or benzyl ether, or as readily cleavable esters such as the acetate. Carboxy groups are often protectable as readily cleavable esters, such as the t-butyl or benzyl ester.

Examples of O-protected hydroxylamines for use in method (a) above include O-benzylhydroxylamine, O-4-methoxybenzylhydroxylamine, O-trimethylsilylhydroxylamine, and O-tert-butoxycarbonylhydroxylamine.

Examples of O,N-diprotected hydroxylamines for use in method (a) above include N,O-bis(benzyl)hydroxylamine, N,O-bis(4-methoxybenzyl) hydroxylamine, N-tert-butoxycarbonyl-O-tert-butyldimethylsilylhydroxylamine, N-tert-butoxycarbonyl-O-tetrahydropyranylhydroxylamine, and N,O-bis(tert-butoxycarbonyl)hydroxylamine.

Compounds of the invention wherein W is an N-formylhydroxylamino group H(C=O)NH(OH)— may be prepared by N-formulation of the corresponding O-protected compound in which W is —NH(OH), then removal of the O-protecting group.

Compounds according to the present invention in which W is a carboxylic acid group —COOH, ie compounds of formula (IIA) or (IIB) above, may be prepared by a process comprising: coupling an acid of formula (III) or an activated derivative thereof

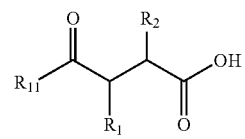

(III)

with an amine of formula (IVA) or (IVB)

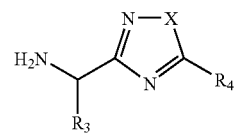

(IVA)

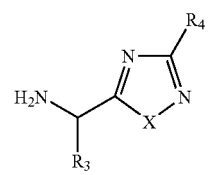

(IVB)

wherein X, $R_1$ $R_2$, $R_3$, and $R_4$ are as defined in general formula (IA) and (IB) except that any substituents in $R_1$, $R_2$, $R_3$, and $R_4$ which are potentially reactive in the coupling reaction may themselves be protected from such reaction, and $R_{11}$ represents a hydroxy protecting group, and subsequently removing the protecting group $R_{11}$ and any protecting groups from $R_1$ $R_2$, $R_3$, and $R_4$.

Active derivatives of acids (III) include activated esters such as the pentafluorophenyl ester, acid anhydrides and acid halides, eg chlorides. Suitable hydroxy protecting groups may be selected from those known in the art.

Compounds of formula (IVA) and (IVB) may be prepared by methods analogous to the general methods for oxadiazole ring formation illustrated in Schemes 1 and 2 in Examples 1 and 2 below.

The following preparative Examples describe the preparation of compounds useful in accordance with the invention.

The following abbreviations have been used in the examples

DCM—Dichloromethane
DMF—N,N-Dimethylformamide
HOBT—1-Hydroxybenzotriazole
Pfp—Pentafluorophenol
WSCDI—N-(3-Dimethylaminopropyl)-N'-ethylcarbodi-imide hydrochloride
HCl—Hydrochloric acid
THF—Tetrahydrofuran
TFA—Trifluoroacetic acid
P(O-Tol)$_3$-Tri-O-tolylphosphine
AcOEt—Ethyl acetate
CH$_3$CN—Acetonitrile

EXAMPLE 1

3R-[2,2-Dimethyl-1S-(5-phenyl-[1,2,4]oxadiazol-3-yl)-propylcarbamoyl]-2S-hydroxy-5-methyl-hexano-hydroxamic acid

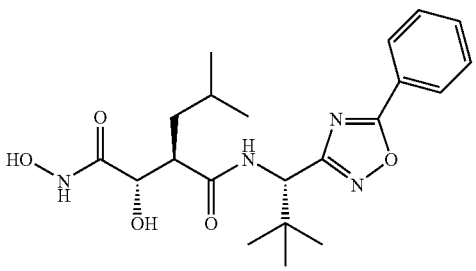

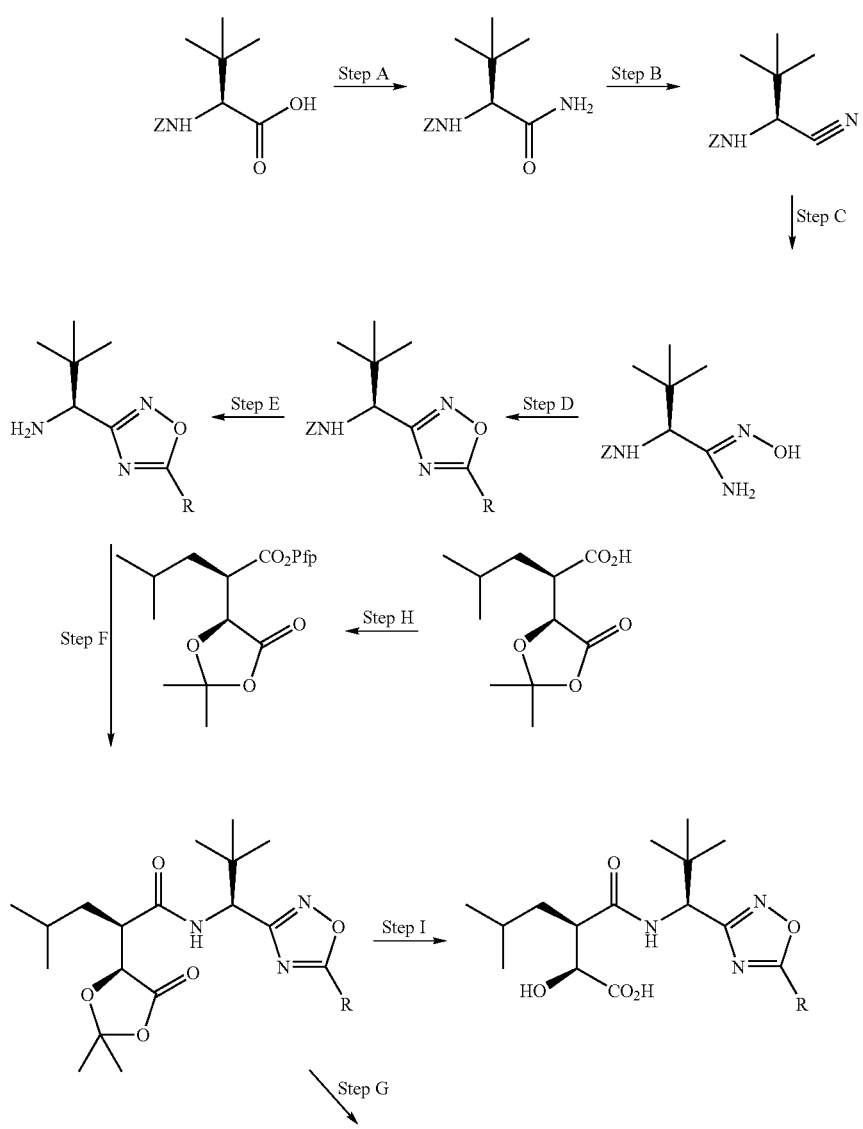

-continued

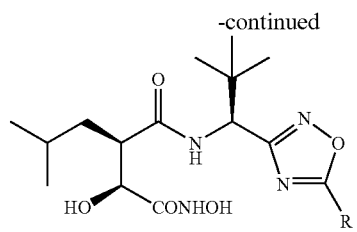

Reagents and conditions. A. HOBT, WSC, NH₃, DMF. B. POCl₃, pyridine. C. Aq.NH₂OH, ethanol, 70° C. D. RCOCl, DMAP, pyridine, DMF, 100° C. E. HBr/acetic acid. F. chiral succinate, DMF. G. Aq.NH₂OH, methanol. H. Pfp, WSC, DMF. I. 1M, HCl, THF.

Example 1 was prepared as outlined in Scheme 1 using procedures described below.

Step A.
(1S-carbamoyl-2,2-dimethyl-propyl)-carbamic acid benzyl ester

N-benzyloxycarbonyl-L-tert-butylglycine (50 g, 189 mmol) was dissolved in DMF (500 mL) and cooled in an ice-water bath before addition of HOBT (28.05 g, 208 mmol) and WSCDI (39.8 g, 208 mmol). Reaction was stirred at 0° C. for 1 hour before addition of 0.880 ammonia solution (21 ml, 377 mmol). The reaction was allowed to warm to room temperature and stirred for 18 hours. DMF was removed under reduced pressure and the residue partitioned between ethyl acetate and 1M HCl. The organic layer was separated and washed with 1M HCl, saturated aqueous sodium bicarbonate solution and brine before drying over magnesium sulphate, filtration and concentration under reduced pressure to yield (1S-carbamolyl-2,2-dimethyl-propyl)-carbamic acid benzyl ester as a white solid (44.1 g, 89%).

1H-NMR; delta (CDCl3), 7.32 (5H, m), 6.05 (1H, bs), 5.71 (1H, bs), 5.60 (1H, d, J=6.5 Hz), 5.08 (2H, s), 4.01 (1H, d, J=6.5 Hz) and 1.00 (9H, s). LRMS; +ve ion 265 (M+H), 287 (M+Na).

Step B. (1S-cyano-2,2-dimethyl-propyl)-carbamic acid benzyl ester (1S-carbamolyl-2,2-dimethyl-propyl)-carbamic acid benzyl ester (44.1 g, 167 mmol) was dissolved in anhydrous pyridine (203 ml, 2.5 mol) under an inert atmosphere and cooled in an ice-water bath. Phosphorus oxychloride (21.8 ml, 234 mmol) was added slowly over 15 minutes and the reaction allowed to stir in the ice water bath for 2 hours before warming to room temperature and stirred for 12 hours. The reaction mixture was treated with ice-water (400 ml) and extracted with ethyl acetate (2×300 ml). The organic layer was separated and washed with 1M HCl, saturated aqueous sodium bicarbonate solution and brine before drying over magnesium sulphate, filtration and concentration under reduced pressure. Column chromatography on silica gel using ethyl acetate/hexane as eluent leads to isolation of the desired product as an orange oil (36.72 g, 89%).

1 H-NMR; delta (CDCl3), 7.42 (5H, m), 5.28 (2H, m), 4.55 (2H, d, J=6.5 Hz) and 1.11 (9H, s), LRMS; +ve ion 269 (M+Na), 247.2 (M+H),

Step C. [1S-(N-hydroxycarbamimidoyl)-2,2-dimethyl-propyl]-carbamic acid benzyl ester (1S-cyano-2,2-dimethyl-propyl)-carbamic acid benzyl ester (37.60 g, 153 mmol) was dissolved in ethanol (300 ml) and treated dropwise with 50% aqueous hydroxylamine (51 ml, 764 mmol). The reaction was heated to reflux and stirred for 3 hours. The reaction was then cooled and concentrated under reduced pressure to yield the desired product as a white foam/gum (41.5 g, 97%).

1 H-NMR; delta (CDCl3), 7.32 (5H, m), 6.21 (1H, bs), 5.95 (1H, bs), 5.81 (1H, d, J=6.4 Hz), 5.08 (2H, m), 4.79 (1H, bs), 4.05 (1H, d, J=6.5 Hz) and 0.95 (9H, s). LRMS; +ve ion 279.8 (M+H).

Step D. [2,2-dimethyl-1S-(5-phenyl-[1,2,4]oxadiazol-3-yl)-propyl]-carbamic acid benzyl ester

[1S-(N-hydroxycarbamimidoyl)-2,2-dimethyl-propyl]-carbamic acid benzyl ester (0.21 g, 0.75 mmol) was dissolved in DMF (5 mL) and treated with pyridine (0.1 ml, 1.28 mmol), benzoyl chloride (0.13 ml, 1.1 mmol) and DMAP (catalytic). The reaction mixture was stirred at room temperature for 4 hour before heating to 100° C. and stirring for 16 hours. The reaction was cooled back to room temperature and concentrated under reduced pressure. The reaction was diluted with ethyl acetate and washed with 1M HCl, saturated aqueous sodium bicarbonate solution and brine before drying over magnesium sulphate, filtration and concentration under reduced pressure. The desired product was isolated as an orange oil (0.22 g, 78%).

1H-NMR; delta (CDCl3), 8.12 (2H, m), 7.55 (3H, m), 7.32 (5H, m), 5.55 (1H, d, J=6.4 Hz), 5.12 (2H, m), 4.95 (1H, d, J=6.5Hz) and 1.10 (9H, s). LRMS; +ve ion 366.2 (M+H), 388.2 (M+Na).

Step E. 2,2-dimethyl-1S-(5-phenyl-[1,2,4]oxadiazol-3-yl)-propylamine

[2,2-dimethyl-1S-(5-phenyl-[1,2,4]oxadiazol-3-yl)-propyl]-carbamic acid benzyl ester (0.2 g, 0.5 mmol) was treated with 48% hydrobromic acid in acetic acid (10 ml). The reaction mixture was stirred at room temperature for 3 hours. The reaction was concentrated under reduced pressure and partitioned between ethyl acetate and 1M Na₂CO₃. The organic layer was further washed with 1M Na₂CO₃ and brine before drying over magnesium sulphate, filtration and concentration under reduced pressure. The product was isolated as a yellow oil (0.13 g, 98%).

LRMS; +ve ion 232 (M+H).

Step F. 2R-(2,2-Dimethyl-5-oxo-[1,3]dioxolan-4S-yl)-4-methyl-pentanoic acid [2,2-dimethyl-1S-(5-phenyl-[1,2,4]oxadiazol-3-yl)-propyl]-amide 2,2-dimethyl-1S-(5-phenyl-[1,2,4]oxadiazol-3-yl)-propylamine (0.13 g, 0.6 mmol) was dissolved in DMF (5 ml) and cooled in an ice-water bath before the addition 2R-(2,2-Dimethyl-5S-oxo-[1,3]dioxolan4-yl)-4-methyl-pentanoic acid pentafluorophenyl ester (0.22 g, 0.6 mmol). Reaction was allowed to warm to room temperature and stirred for 15 hours. The DMF was removed under reduced pressure and the reaction diluted with ethyl acetate and washed with 1M HCl, saturated aqueous sodium bicarbonate solution and brine before drying over magnesium sulphate, filtration and concentration under reduced pressure. Column chromatography on silica gel using ethyl acetate and hexane (1:1) lead to isolation of the desired product as a white solid (0.16 g, 64%).

1H-NMR; delta (CDCl3), 8.12 (2H, m), 7.55 (3H, m), 6.65 (1H, d, J=6.4 Hz), 5.25 (1H, d, J=6.5 Hz), 4.55 (1H, d, J=5.9 Hz), 2.75 (1H, m), 1.64 (3H, s), 1.55 (3H, s), 1.04 (9H, s) and 0.88 (6H, m). LRMS; +ve ion 444 (M+H).

Step G. 3R-[2,2-Dimethyl-1S-(5-phenyl-[1,2,4]oxadiazol-3-yl)-propylcarbamoyl]-2S-hydroxy-5-methyl-hexanohydroxamic acid 2R-(2,2-Dimethyl-5S-oxo-[1,3]dioxolan-4-yl)-4-methyl-pentanoic acid [2,2-dimethyl-1S-(5-phenyl-[1,2,4]oxadiazol-3-yl)-propyl]-amide (0.05 g, 0.11 mmol) was dissolved in methanol (2 ml) and treated with 50% aqueous hydroxylamine (0.04 ml, 0.5 mmol). Reaction was stirred at room temperature for 2 hours before evaporation under reduced pressure. The reaction product was separated by preparative reverse phase chromatography to yield the required product as a white solid (0.02 g, 44%).

1H-NMR; delta (CH3OD), 8.13 (2H, m), 7.65 (1H, m), 7.58 (2H, m), 5.14 (1H, s), 4.01 (1H, d, J=7.1 Hz), 2.94 (1H, m), 1.60 (1H, m), 1.45 (1H, m), 1.16 (1H, m), 1.07 (9H, s), 0.89 (3H, d, J=6.5 Hz) and 0.86 (3H, d, J=6.6 Hz). 13 C-NMR; delta (CH3OD), 177.1, 176.3, 172.0, 171.6, 134.6, 130.8, 129.4, 125.7, 73.7, 55.8, 49.6, 39.7, 36.2, 27.4, 27.2, 24.2 and 22.5. LRMS; +ve ion 419 (M+H); −ve ion 417 (M−H).

Step H. 2R-(2,2-Dimethyl-5-oxo-[1,3]dioxolan-4S-yl)-4-methyl-pentanoic acid pentafluorophenyl ester 2R-(2,2-Dimethyl-5-oxo-[1,3]dioxolan-4S-yl)-4-methyl-pentanoic acid (prepared according to WO 94/02447) (30 g, 130 mmol) was dissolved in ethyl acetate (300 ml) and treated with pentafluorophenol (28.8 g, 156 mmol) and WSCDI (30 g, 156 mmol). Reaction was heated to reflux for 2 hours and then allowed to stir at room temperature for 12 hours. The reaction mixture was washed with 1M Na2CO3 and brine before drying over magnesium sulphate, filtration and concentration under reduced pressure. The product was recrystallised from ethyl acetate/hexane to yield the desired product as a single diastereomer (21.2 g, 42%).

1H-NMR; delta (CDCl3), 4.55 (1H, d, J=6.7 Hz), 3.31 (1H, m), 1.85 (3H, bm), 1.65 (3H, s), 1.58 (3H, s), 1.05 (3H, d, J=6.5 Hz) and 0.99 (3H, d, J=6.5 Hz).

Also prepared, the diastereomer 3R-[2,2-dimethyl-1S-(5-phenyl-[1,2,4]oxadiazol-3-yl)-propylcarbamoyl]-2R-hydroxy-5-methyl-hexanohydroxamic acid.

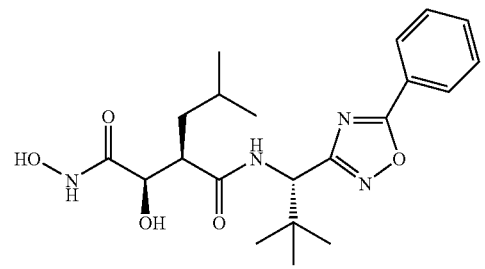

M+H=420.0, M+Na=441.5, M−H=417.5.

The corresponding carboxylic acid was prepared as outlined in Scheme 1 and the procedure below.

Step I. 3R-[1S-(5-Furan-2-yl-[1,2,4]oxadiazol-3-yl)-2,2-dimethyl-propylcarbamoyl]-2S-hydroxy-5-methyl-hexanoic acid 2R-(2,2-Dimethyl-5S-oxo-[1,3]dioxolan-4-yl)-4-methyl-pentanoic acid [2,2-dimethyl-1S-(5-Furan-2-yl-[1,2,4]oxadiazol-3-yl)-propyl]-amide (0.05 g, 0.12 mmol) was dissolved in tetrahydrofuran (5 ml) and cooled to 4° C. during the addition of 1M hydrochloric acid (5 ml). The solution was allowed to warm to room temperature and then stirred for 18 hours. The bulk of the solvent was removed under reduced pressure before drying under high vacuum to a white foam (0.045 g, ca. quant.).

1H-NMR; delta (CH3OD), 7.88 (1H, s), 7.45 (1H, d, J=3.6 Hz), 6.74 (1H, m), 5.15 (1H, s), 4.18 (2H, d, J=6.4 Hz), 2.91 (1H, m), 1.65 (1H, m), 1.50 (1H, m), 1.31 (1H, m), 1.06 (9H, s), 0.88 (3H, d, J=6.4 Hz) and 0.82 (3H, d, J=6.5 Hz). LRMS; −ve ion 392.2 (M−H).

EXAMPLE 2

3R-[2,2-Dimethyl-1S-(3-phenyl-[1,2,4]oxadiazol-5-yl)-propylcarbamoyl]-2S-hydroxy-5-methyl-hexanohydroxamic acid

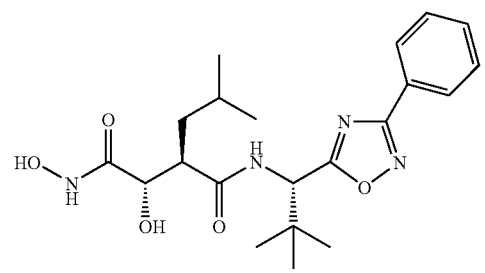

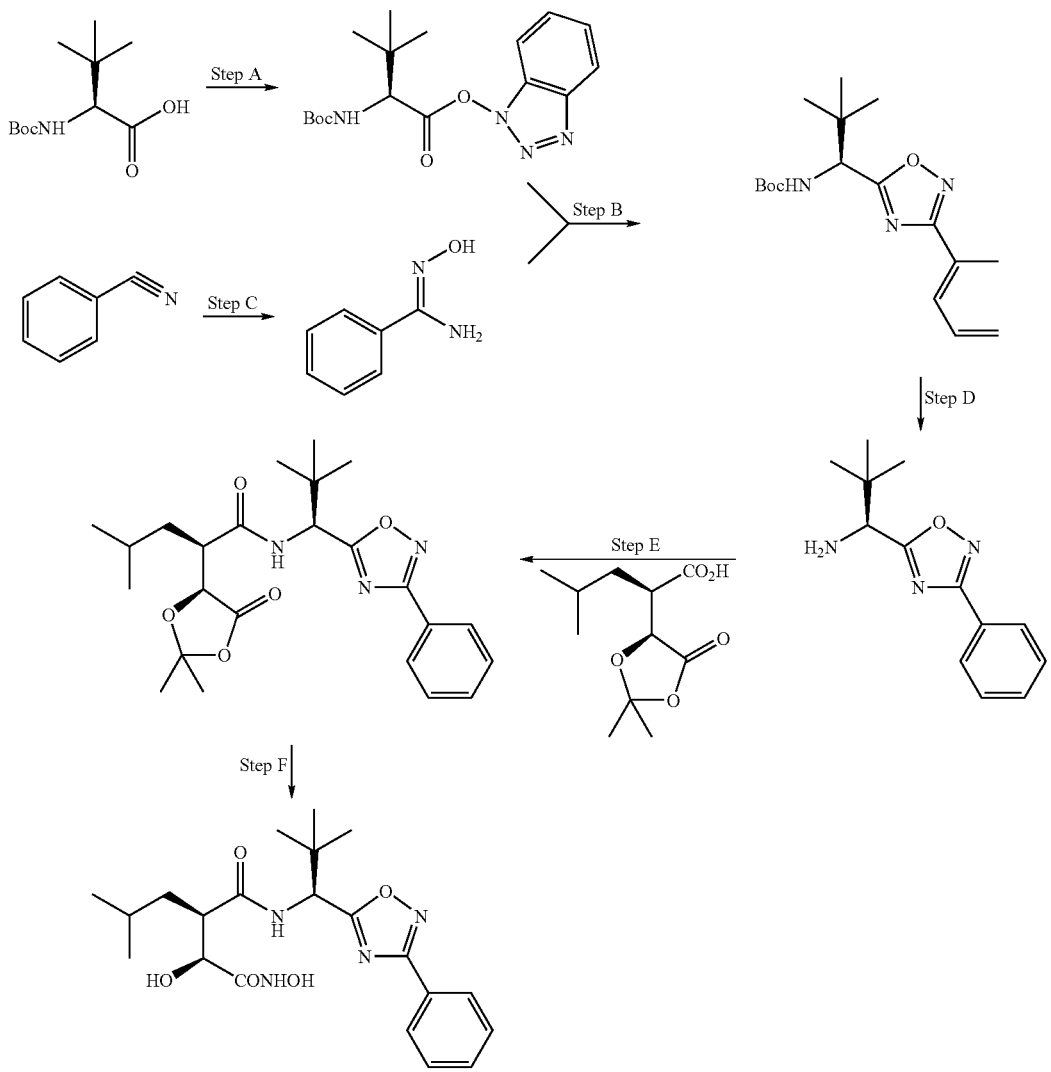

Reagents and conditions. A. HOBT, WSCDI, DMF. B. Toluene, 100° C. C. Aq.NH₂OH, ethanol, 70° C. D. TFA, DCM. E. HOBT, WSCDI, DMF. F. Aq.NH₂OH, methanol.

Example 2 was prepared as outlined in scheme 2 using procedures described below.

Step A.
2S-tert-Butoxycarbonylamino-3,3-dimethyl-butyric acid benzotriazol-1-yl ester A solution of N-tert-Butoxycarbonyl-L-tert-butyl glycine (5 g, 21.6 mmol) in ethyl acetate (80 mL) was cooled in an ice-water bath. HOBT (3.22 g, 23.8 mmol) and WSCDI (4.56 g, 23.8 mmol) were added and the reaction allowed to stir at room temperature for 12 hours. The reaction mixture was washed with 1M $Na_2CO_3$ and brine, before drying over magnesium sulphate, filtration and concentration to a white foam (5.74 g, 76%).

1H-NMR; delta (CDCl3), 8.05 (1H, m), 7.65 (2H, m), 7.41 (1H, m), 5.10 (1H, d, J=6.7 Hz), 4.45 (1H, d, J=6.5 Hz), 1.55 (9H, s) and 1.21 (9H, s). LRMS; +ve ion 349 (M+H).

Step B. [2,2-Dimethyl-1S-(3-phenyl-[1,2,4]oxadiazol-5-yl)-propyl]-carbamic acid tert-butyl ester 2S-tert-Butoxycarbonylamino-3,3-dimethyl-butyric acid benzotriazol-1-yl ester (3.71 g, 10.7 mmol) was dissolved in toluene (80 mL) and treated with N-hydroxy-benzamidine (2.9 g, 21.3 mmol). The reaction mixture was stirred at 110° C. for 18 hours. The solution was concentrated under reduced pressure and partitioned between ethyl acetate and 1M $Na_2CO_3$. The organic layer was further washed with 1M $Na_2CO_3$ and brine before drying over magnesium sulphate, filtration and concentration under reduced pressure. Column chromatography on silica gel using ethyl acetate and hexane (1:4) lead to isolation of the desired product (2.58 g, 73%).

1H-NMR; delta (CDCl3), 8.10 (2H, m), 7.50 (3H, m), 5.30 (1H, bd), 4.95 (1H, d, J=6.5 Hz), 1.44 (9H, s) and 1.03 (9H, s). LRMS; +ve ion 354.2 (M+Na).

Step C. N-hydroxy-benzamidine

Benzonitrile (5 g, 48 mmol) was dissolved in ethanol (100 ml) and treated with 50% aqueous hydroxylamine (16 ml, 242 mmol). Reaction was heated to reflux for 3 hours before concentration under reduced pressure to give a clear foam (4.5 g, 68%).
LRMS; +ve ion 137 (M+H).

Step D. 2,2-Dimethyl-1S-(3-phenyl-[1,2,4]oxadiazol-5-yl)-propylamine

[2,2-Dimethyl-1S-(3-phenyl-[1,2,4]oxadiazol-5-yl)-propyl]-carbamic acid tert-butyl ester (1 g, 3.0 mmol) was dissolved in DCM (5 ml) and treated with TFA (5 ml). Reaction stirred at room temperature for 3 hours. The reaction was concentrated under reduced pressure and partitioned between ethyl acetate and 1M $Na_2CO_3$. The organic layer was further washed with 1M $Na_2CO_3$ and brine before drying over magnesium sulphate, filtration and concentration under reduced pressure to give the desired product (0.65 g, 93%).
1H-NMR; delta (CH3OD), 8.10 (2H, m), 7.55 (3H, m), 4.81 (1H, s) and 1.19 (9H, s). LRMS; +ve ion 232 (M+H).

Step E. 2R-(2,2-Dimethyl-5-oxo-[1,3]dioxolan-4S-yl)-4-methyl-pentanoic acid-[2,2-dimethyl-1S-(3-phenyl-[1,2,4]oxadiazol-5-yl)-propyl]-amide 2R-(2,2-Dimethyl-5-oxo-[1,3]dioxolan-4S-yl)4-methyl-pentanoic acid (0.27 g, 1.17 mmol) was dissolved in DMF (5 ml) and cooled in an ice-water bath before addition of HOBT (0.17 g, 1.29 mmol) and WSCDl (0.25 g, 1.29 mmol). Reaction was stirred at 0° C. for 1 hour before addition of 2,2-Dimethyl-1S-(3-phenyl-[1,2,4]oxadiazol-5-yl)-propylamine (0.3 g, 1.29 mmol). The reaction was allowed to warm to room temperature and stirred for 18 hours. DMF was removed under reduced pressure and the residue partitioned between ethyl acetate and 1M HCl. The organic layer was separated and washed with 1M HCl, saturated aqueous sodium bicarbonate solution and brine before drying over magnesium sulphate, filtration and concentration under reduced pressure. Column chromatography on silica gel using ethyl acetate and hexane (1:4) lead to isolation of the desired product (0.26 g, 46%).
1H-NMR; delta (CDCl3), 8.10 (2H, m), 7.50 (3H, m), 6.80 (1H, d, J=9.3 Hz), 5.24 (1H, d, J=9.3 Hz), 4.55 (1H, d, J=5.1 Hz), 2.81 (1H, m), 1.63 (3H, 1.55 (3H, s), 0.92 (3H, d, J=6.1 Hz) and 0.89 (3H, d, J=6.2 Hz). LRMS; +ve ion 444 (M+H).

Step F. 3R-[2,2-Dimethyl-1S-(3-phenyl-[1,2,4]oxadiazol-5-yl)-propylcarbamoyl]-2S-hydroxy-5-methyl-hexanohydroxamic acid 2R-(2,2-Dimethyl-5-oxo-[1,3]dioxolan4S-yl)-4-methyl-pentanoic acid [2,2-dimethyl-1S-(3-phenyl-[1,2,4]oxadiazol-5-yl)-propyl]-amide (0.26 g, 0.6 mmol) was dissolved in methanol (5 ml) and treated with 50% aqueous hydroxylamine (0.2 ml, 2.95 mmol). Reaction stirred at room temperature for 3 hrs before concentration under reduced pressure. The product was recrystallised from ethyl acetate/hexane to yield the desired product (0.11 g, 41%).
1H-NMR; delta(CH3OD), 8.06 (2H, m), 7.53 (3H, m), 5.21 (1H, s), 4.01 (1H, d, J=7.5Hz), 2.99 (1H, m), 1.60 (1H, m), 1.50 (1H, m), 1.15 (1H, m), 1.10 (9H, s), 0.92 (3H, d, J=6.6 Hz) and 0.81 (3H, d, J=6.5 Hz). 13 C-NMR; delta (CH3OD), 180.3, 176.7, 172.0, 169.7, 132.9, 130.5, 128.8, 128.4, 73.7, 57.1, 49.5, 39.5, 36.5, 27.3, 24.3 and 22.5. LRMS; +ve ion 419 (M+H); –ve ion 417 (M–1).

EXAMPLE 3

2R-[3-(4-Ethoxy-phenyl)-propyl]-$N_1$-[1S-(5-thiophen-2-yl)-[1,2,4]oxadiazol-3-yl)-2,2-dimethyl-propyl]-3S,$N_4$-dihydroxy-succinamide

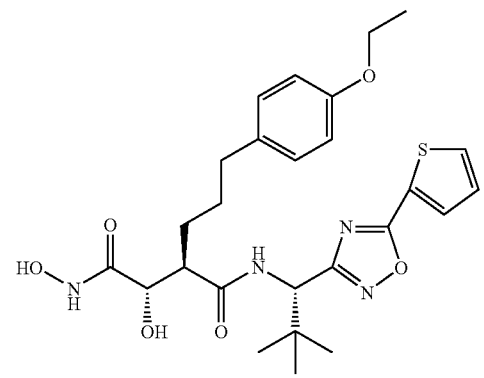

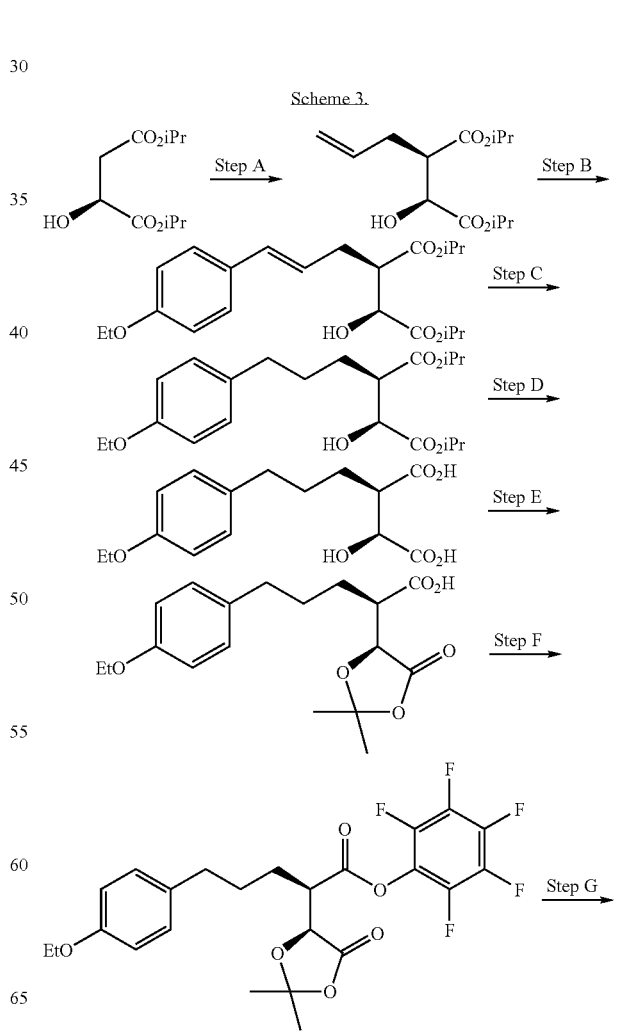

-continued

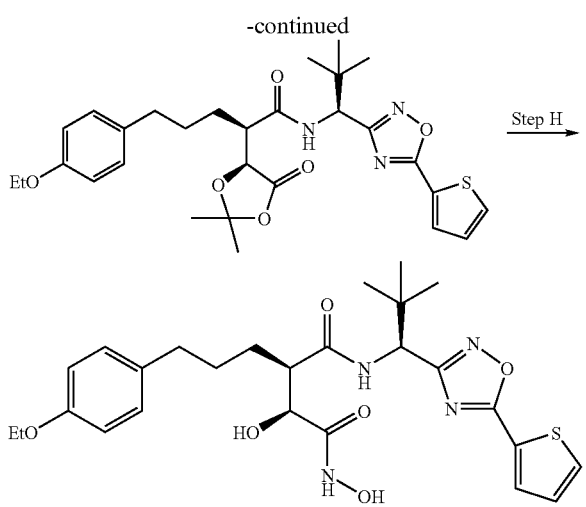

Reagents and conditions. A. LiHMDS, AllBr, THF, -78 to RT; B: 4-OEt-phenylBr, P(o-Tol)₃, Pd(OAc)₂, NEt₃, CH₃CN; C: 10%Pd/C, H₂, MeOH; D: LiOH, MeOH, H₂O; E: CuCl₂, dimethoxyacetone, acetone; F: pentafluorophenol, WSC, HOAt, CH₂Cl₂; G: Amine (as detailed in Step E, Scheme 1), DMF; H: aq.NH₂OH, iPrOH Example 3 was prepared as outlined in Scheme 3 using procedures described below.

Step A: 2R-allyl-3S-hydroxy-succinic acid diisopropylester

To a cold (−78 C) solution of 2S-Hydroxy-succinic acid diisopropyl ester (19.70 ml, 95 mmol) in THF (35 ml) was added LiHMDS (200 ml, 0.2 mol, 2.1 eq.) dropwise. The reaction mixture was stirred at −78 C for two hours and then at −30 C for 30 min. The reaction mixture was then cooled to −78 C and allyl bromide (12.36 ml, 0.14 mol, 1.5 eq.) was added dropwise. The reaction mixture was allowed to warm to RT overnight. It was poured into a saturated solution of NH₄Cl/ice (200 ml). Extraction with AcOEt (3×200 ml) followed by a wash with water (50 ml) and with brine (50 ml) afforded a yellow oil after removal of the solvents under vacuum. Purification by flash chromatography gave 2R-allyl-3S-hydroxy-succinic acid diisopropylester as a colourless oil (7.76 g, de=80%, 40% yield).

1H-NMR; delta (CDCl₃), 5.77-5.88 (1H, m), 4.98-5.21 (4H, m), 4.22 (1H, brs), 3.18 (1H, bs), 2.87-2.94 (1H, m), 2.56-2.65 (1H, m), 2.40-2.48 (1H, m), 1.29 (6H, d, J=6.3 Hz) and 1.22 (6H, d, J=6.3 Hz). LRMS: +ve ion 281 (M+Na).

Step B: 2R-[3-(4-ethoxy-phenyl)-allyl]-3S-hydroxy-succinic acid diisopropyl ester To a solution of 2R-allyl-3S-hydroxy-succinic acid diisopropylester (4.79 g, 18.5 mmol), 4-bromo phenetole (3.19 ml, 22.2 mmol, 1.2 eq.) and NEt₃ (6.22 ml, 44.6 mmol, 2.4 eq.) in CH₃CN (40 ml), was added a sonicated (for 2 min) suspension of P(O-Tol)₃ (0.57 g, 2.22 mmol, 0.1 eq.) and Pd(OAc)₂ (209 mg, 5%) in CH₃CN (5 ml). The reaction mixture was heated to reflux for 2 hrs. CH₃CN was removed under vacuum. The crude was extracted with AcOEt (3×200 ml), washed with water (50 ml) and with brine (50 ml). A purification by flash chromatography afforded the desired 2R-[3-(4-ethoxy-phenyl)-allyl]-3S-hydroxy-succinic acid diisopropyl ester (5.92 g, 84% yield).

1H-NMR; delta (CDCl₃), 7.28 (2H, d, J=8.8 Hz), 6.83 (2H, d, J=8.8 Hz), 6.46 (1H, d, J=15.7 Hz), 6.02-6.12 (1H, m), 4.98-5.13 (2H, m), 4.26 (1H, dd, J=7.1, 3.0 Hz), 4.02 (2H, q, J=7.0 Hz), 3.23 (1H, d, J=7.1 Hz), 2.92-2.97 (1H, m), 2.68-2.79 (1H, m), 2.49-2.62 (1H, m), 1.41 (3H, t, J=7.0 Hz) and 1.19-1.30 (12H, m). LRMS: +ve ion 400 (M+Na).

Step C: 2R-[3-(4-ethoxy-phenyl)-propyl]-3S-hydroxy-succinic acid diisopropyl ester To a solution of 2R-[3-(4-ethoxy-phenyl)-allyl]-3S-hydroxy-succinic acid diisopropyl ester (129 mg, 0.34 mmol) in MeOH (10 ml) under an inert atmosphere, was added 10% Pd/C (13 mg). H₂ was bubbled through the resulting suspension for 30 min. The reaction mixture was then stirred under 1 atmosphere of H₂ for 16 hrs. Pd/C was filtered off and the solvent removed under reduced pressure to give 2R-[3-(4-ethoxy-phenyl)-propyl]-3S-hydroxy-succinic acid diisopropyl ester (115 mg, 88% yield).

1H-NMR; delta (CDCl₃), 7.08 (2H, d, J=8.6 Hz), 6.81 (2H, d, J=8.6 Hz), 4.97-5.14 (2H, m), 4.20 (1H, dd, J=7.3, 3.5 Hz), 4.01 (2H, q, J=7.0 Hz), 3.18 (1H, d, J=7.3 Hz), 2.77-2.83 (1H, m), 2.55-2.62 (2H, m), 1.45-1.94 (4H, m), 1.40 (3H, t, J=7.0 Hz) and 1.12-1.30 (12H, m). LRMS: +ve ion 402.0 (M+Na).

Step D: 2R-[3-(4-ethoxy-phenyl)-propyl]-3S-hydroxy-succinic acid

To a solution of 2R-[3-(4-ethoxy-phenyl)-propyl]-3S-hydroxy-succinic acid diisopropyl ester (4.78 g, 12.6 mmol) in THF/water (3:1, 120 ml) was added NaOH (1.66 g, 41.5 mmol, 5.5 eq.). The reaction mixture was then stirred for 16 hrs at RT. The mixture was concentrated under reduced pressure and acidify to pH=3 by addition of HCl 1N. The hydroxy diacid was extracted with AcOEt. The organic layer was dried over MgSO₄ and the solvent removed under reduced pressure to give the desired 2R-[3-(4-ethoxy-phenyl)-propyl]-3S-hydroxy-succinic acid (3.66 g, 85% yield).

1H-NMR; delta (CH3OD), 7.07 (2H, d, J=8.6 Hz), 6.79 (2H, d, J=8.6 Hz), 4.23 (1H, d, J=5.8 Hz), 3.98 (2H, q, J=7.0 Hz), 2.76-2.81 (1H, m), 2.53-2.59 (2H, m), 1.55-1.72 (4H, m), 1.35 (3H, t, J=7.0 Hz). LRMS: +ve ion 319 (M+Na); −ve ion 295 (M−H).

Step E: 2R-(2,2-dimethyl-5-oxo-[1,3]dioxolan-4S-yl)-5-(4-ethoxy-phenyl)-pentanoic acid To a solution of 2R-[3-(4-ethoxy-phenyl)-propyl]-3S-hydroxy-succinic acid (3.66 g, 12.3 mmol) in acetone (50 ml) under an inert atmosphere were added dimethoxy propane (2.58 ml, 21 mmol, 1.7 eq.) and copper chloride (165 mg, 1.2 mmol, 0.1 eq.). The reaction mixture was stirred at RT for 16 hrs. The solvent was then removed under vacuum to give 2R-(2,2-dimethyl-5-oxo-[1,3]dioxolan-4S-yl)-5-(4-ethoxy-phenyl)-pentanoic acid (4.03 g, 97% yield).

¹H-NMR; delta (CDCl₃), 7.08 (2H, d, J=8.5 Hz), 6.82 (2H, d, J=8.5 Hz), 4.48 (1H, d, J=4.8 Hz), 4.01 (2H, q, J=7.0 Hz), 2.91-2.98 (1H, m), 2.54-2.64 (3H, m), 1.23-2.20 (4H, m), 1.58 (3H, s), 1.53 (3H, s) and 1.40 (3H, t, J=7.0 Hz). LRMS: +ve ion 359 (M+Na); −ve ion 335 (M−H).

Step F. 2R-(2,2-dimethyl-5-oxo-[1,3]dioxolan4S-yl)-5-(4-ethoxy-phenyl)-pentanoic acid pentafluorophenyl ester To a cold (0° C.) solution of 2R-(2,2-dimethyl-5-oxo-[1,3]dioxolan-4S-yl)-5-(4-ethoxy-phenyl)-pentanoic acid (4.03 g, 12 mmol) and pentafluoro phenol (2.43 g, 13.2 mmol, 1.1 eq.) in CH$_2$Cl$_2$ (50 ml) was added WSC (2.54 g, 13.2 mmol, 1.1 eq.). The reaction mixture was allowed to warm to RT overnight. CH$_2$Cl$_2$ was removed under vacuum, and the resulting crude reaction mixture was dissolved in AcOEt (200 ml). The organic layer was washed with water (50 ml), NaHCO$_3$ $_{sat}$ (20 ml) and finally with brine (20 ml). Solvent was removed under reduced pressure to give an oil which was purified by flash chromatography to furnish the expected 2R-(2,2-dimethyl-5-oxo-[1,3]dioxolan-4S-yl)-5-(4-ethoxy-phenyl)-pentanoic acid pentafluorophenyl ester (3.94 g, 65% yield).

1H-NMR; delta (CDCl$_3$), 7.09 (2H, d, J=8.4 Hz), 6.83 (2H, d, J=8.4 Hz), 4.56 (1H, d, J=6.0 Hz), 4.01 (2H, q, J=7.0 Hz), 3.20-3.28 (1H, m), 2.64 (2H, t, J=7.6 Hz), 1.98-2.08 (2H, m), 1.70-1.86 (2H, m), 1.62 (3H, s), 1.57 (3H, s) and 1.40 (3H, t, J=7.0 Hz).

Step G. 2R-[3-(4-Ethoxy-phenyl)-propyl]-N$_1$-[1S-(5-thiophen-2-yl)-[1,2,4]oxadiazol-3-yl)-2,2-dimethyl-propyl]-[1,3]dioxolan-4S-one To a solution of 2R-(2,2-dimethyl-5-oxo-[1,3]dioxolan4S-yl)-5-(4-ethoxy-phenyl)-pentanoic acid pentafluorophenyl ester (150 mg, 0.30 mmol) in CH$_2$Cl$_2$ (10 ml) was added 2,2-dimethyl-1S-(5-thiophen-2-yl)-[1,2,4]oxadiazol-3-yl)-propylamine (100 mg, 0.42 mmol, 1.4 eq.). The reaction mixture was stirred for 16 hrs and the solvent was removed under vacuum. The crude was taken-up in AcOEt (70 ml) and washed with water (10 ml), then with Na$_2$CO$_3$ (10 ml) and finally with brine (10 ml). The solvent was dried over MgSO$_4$ and removed under reduced pressure to give the desired 2R-[3-(4-Ethoxy-phenyl)-propyl]-N$_1$-[1S-(5-thiophen-2-yl)-[1,2,4]oxadiazol-3-yl)-2,2-dimethyl-propyl]-[1,3]dioxolan-4S-one (82 mg, 33% crude).

1 H-NMR; delta (CDCl$_3$), 7.88 (1H, m), 7.62 (1H, m), 7.20 (1H, m), 6.95 (2H, d, J=8.4 Hz), 6.71 (2H, d, J=8.4 Hz), 6.55 (1H, d, J=9.7 Hz), 5.19 (1H, d, J=9.7 Hz), 4.56 (1H, d, J=6.4 Hz), 3.95 (2H, q, J=7.0 Hz), 2.64 (3H, bm), 1.84 (2H, m), 1.70 (2H, m), 1.62 (3H, s), 1.54 (3H, s), 1.38 (3H, t, J=6.9 Hz) and 1.02 (9H, s). LRMS: +ve ion 556.0 (M+H).

Step H. 2R-[3-(4-Ethoxy-phenyl)-propyl]-N$_1$-[1S-(5-thiophen-2-yl)-[1,2,4]oxadiazol-3-yl)-2,2-dimethyl-propyl]-3S,N$_4$-dihydroxy-succinamide To a solution of 2R-[3-(4-Ethoxy-phenyl)-propyl]-N$_1$-[1S-(5-thiophen-2-yl)-[1,2,4]oxadiazol-3-yl)-2,2-dimethyl-propyl]-[1,3]dioxolan4S-one (82 mg, 0.15 mmol) in i-PrOH (5 ml), was added an aqueous solution of hydroxylamine (50%, 48 μl, 0.7 mmol, 5 eq.). The reaction mixture was allowed to stir at RT for 16 hrs. The solvent was removed under reduced pressure to yield an oil which was purified by preparative reverse phase chromatography to give the required product (25.3 mg, 32%).

1H-NMR; delta(CH3OD),1H-NMR; delta(CH3OD), 7.86 (2H, m), 7.25 (1H, dd, J=3.8Hz), 6.83 (2H, d, J=8.6Hz), 6.54 (2H, d, J=8.6Hz), 5.14 (1H, s), 4.03 (1H, d, J=7.6 Hz), 3.87 (2H, q, J=6.96), 2.88 (1H, m), 2.45 (2H, bm), 1.53 (4H, bm), 1.33 (3H, t, J=7.0 Hz) and 1.06 (9H, s). LRMS: +ve ion 553.2 (M+Na); −ve ion 529.2 (M−H)

The compounds of Examples 4-17 were prepared by the method of Example 1 by parallel synthesis, using the appropriate acid chloride in Step D. The products were purified by preparative HPLC:

EXAMPLE 4

2S-Hydroxy-3R-[1S-(5-isopropyl-[1,2,4]oxadiazol-3-yl)-2,2-dimethyl-propylcarbamoyl]-5-methyl hexanohydroxamic acid

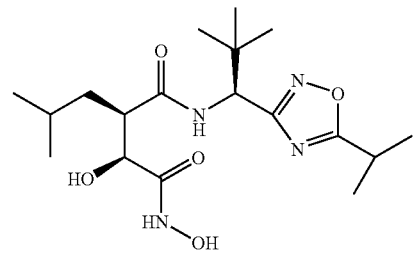

LRMS; +ve ion 407 (M+Na); −ve ion 383 (M−H)

EXAMPLE 5

2S-Hydroxy-3R-[1S-(5-furan-2-yl-[1,2,4]oxadiazol-3-yl)-2,2-dimethyl-propylcarbamoyl]-5-methyl hexanohydroxamic acid

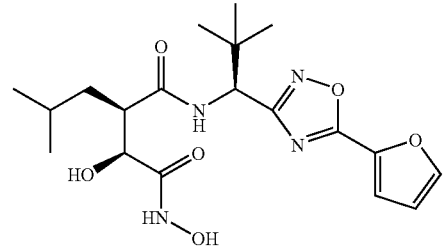

LRMS; +ve ion 431 (M+Na), −ve ion 407 (M−H).

EXAMPLE 6

2S-Hydroxy-3R-[1S-(5-cyclopentylmethyl-[1,2,4]oxadiazol-3-yl)-2,2-dimethyl-propylcarbamoyl]-5-methyl hexanohydroxamic acid

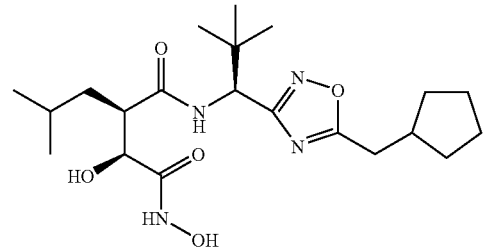

LRMS; +ve ion 425 (M+H), −ve ion 423 (M−H).

EXAMPLE 7

2S-Hydroxy-3R-[1S-(5-thiopen-2-ylmethyl-[1,2,4]oxadiazol-3-yl)-2,2-dimethyl-propylcarbamoyl]-5-methyl hexanohydroxamic acid

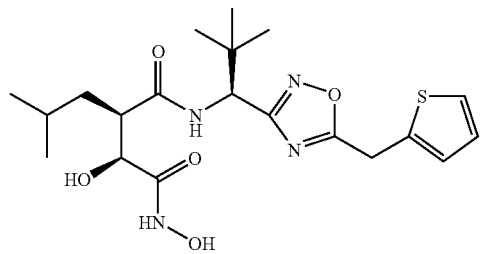

LRMS; +ve ion 461 (M+Na), −ve ion 437 (M−H).

EXAMPLE 8

2S-Hydroxy-3R-[1S-(5-ethyl-[1,2,4]oxadiazol-3-yl)-2,2-dimethyl-propylcarbamoyl]-5-methyl hexanohydroxamic acid

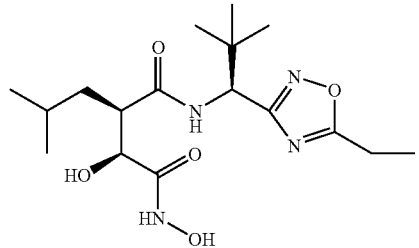

LRMS; +ve ion 393 (M+Na), −ve ion 369 (M−H).

EXAMPLE 9

2S-Hydroxy-3R-[1S-(5-cyclopentyl-[1,2,4]oxadiazol-3-yl)-2,2-dimethyl-propylcarbamoyl]-5-methyl hexanohydroxamic acid

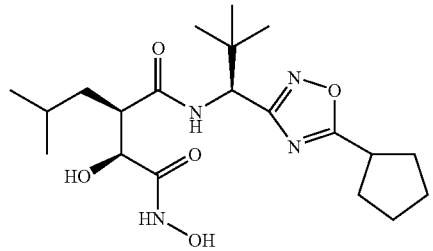

LRMS; +ve ion 411 (M+H), −ve ion 409 (M−H).

EXAMPLE 10

2S-Hydroxy-3R-[1S-(5-benzyl-[1,2,4]oxadiazol-3-yl)-2,2-dimethyl-propylcarbamoyl]-5-methyl hexanohydroxamic acid

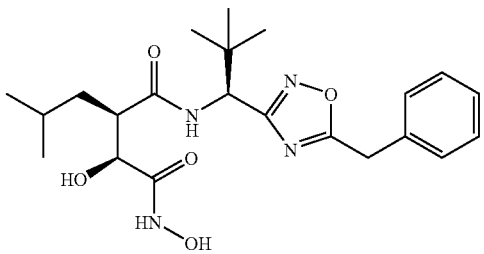

LRMS; +ve ion 433 (M+H), −ve ion 431 (M−H).

EXAMPLE 11

2S-Hydroxy-3R-[1S-(5-isobutyl-[1,2,4]oxadiazol-3-yl)-2,2-dimethyl-propylcarbamoyl]-5-methyl hexanohydroxamic acid

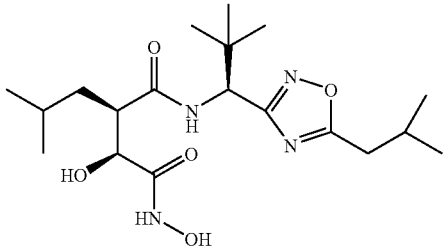

LRMS; +ve ion 421 (M+Na), −ve ion 397 (M−H).

EXAMPLE 12

2S-Hydroxy-3R-[1S-(5-tert-butyl-[1,2,4]oxadiazol-3-yl)-2,2-dimethyl-propylcarbamoyl]-5-methyl hexanohydroxamic acid

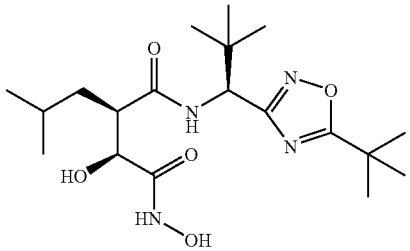

LRMS; +ve ion 421 (M+Na), −ve ion 397 (M−H).

EXAMPLE 13

2S-Hydroxy-3R-[1S-(5-thiophen-2-yl-[1,2,4]oxadiazol-3-yl)-2,2-dimethyl-propylcarbamoyl]-5-methyl hexanohydroxamic acid

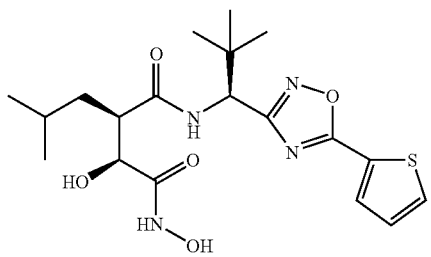

LRMS; +ve ion 425 (M+H), −ve ion 423 (M−H).

Also prepared, the diastereomer 2R-hydroxy-3R-[1S-(5-thiophen-2-yl-[1,2,4]oxadiazol-3-yl)-2,2-dimethyl-propylcarbamoyl]-5-methyl hexanohydroxamic acid

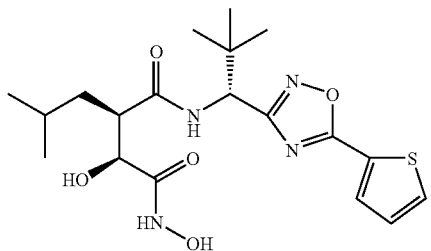

M+H=425.1, M+Na=447.1, M−H=423.0.

EXAMPLE 14

2S-Hydroxy-3R-[1S-(5-(2,2-dimethyl-propyl)-[1,2,4]oxadiazol-3-yl)-2,2-dimethyl-propylcarbamoyl]-5-methyl hexanohydroxamic acid

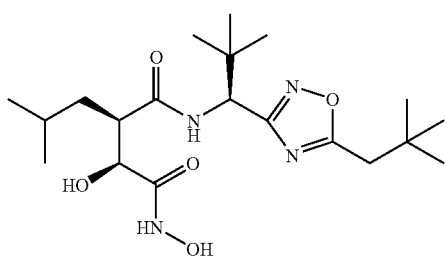

LRMS; +ve ion 435 (M+Na), −ve ion 411 (M−H).

EXAMPLE 15

2S-Hydroxy-3R-[1S-(5-p-tolyl-[1,2,4]oxadiazol-3-yl)-2,2-dimethyl-propylcarbamoyl]-5-methyl hexanohydroxamic acid

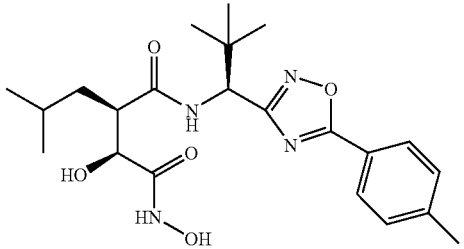

LRMS; +ve ion 433 (M+H), −ve ion 431 (M−H).

EXAMPLE 16

2S-Hydroxy-3R-[1S-(5-cyclopropyl-[1,2,4]oxadiazol-3-yl)-2,2-dimethyl-propylcarbamoyl]-5-methyl hexanohydroxamic acid

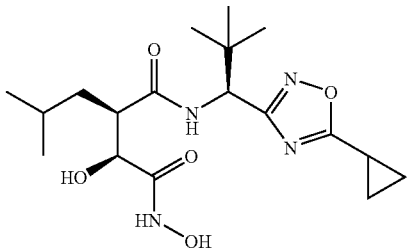

LRMS; +ve ion 405 (M+Na), −ve ion 381 (M−H).

EXAMPLE 17

2S-Hydroxy-3R-[1S-(5-methyl-[1,2,4]oxadiazol-3-yl)-2,2-dimethyl-propylcarbamoyl]-5-methyl hexanohydroxamic acid

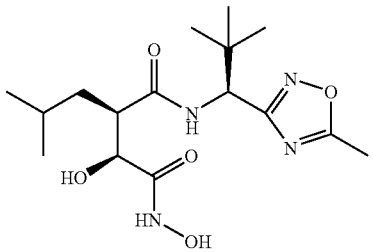

1H-NMR; delta(CH3OD), 8.26 (1H, d, J=9.4 Hz), 5.02 (1H, d, J=9.5 Hz), 4.02 (1H, d, J=6.4 Hz), 2.89 (1H, m), 2.57 (3H, s), 1.61 (1H, m), 1.44 (1H, m), 1.22 (1H, m), 1.00 (9H, s) 13 C-NMR; delta (CH3OD), 178.6, 176.1, 171.9, 170.7, 73.5, 55.6, 49.5, 39.9, 36.2, 27.6, 26.6, 24.2, 22.7 and 12.4. LRMS; +ve ion 379 (M+Na), −ve ion 355 (M−H).

The compounds of Examples 18-19 were prepared by the method of Example 2, by using the appropriate nitrile in Step C and/or the appropriate amino acid residue in Step A:

EXAMPLE 18

2S-Hydroxy-3R-[1S-(3-isopropyl-[1,2,4]oxadiazol-3-yl)-2,2-dimethyl-propylcarbamoyl]-5-methyl hexanohydroxamic acid

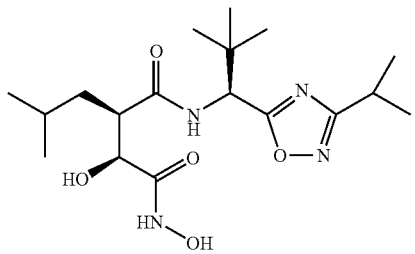

1H-NMR; delta(CH3OD), 5.12 (1H, s), 3.98 (1H, d, J=7.5 Hz), 3.06 (1H, m), 2.92 (1H, m), 1.61 (1H, m), 1.43 (1H, m), 1.31 (6H, d, J=6.9 Hz), 1.14 (1H, m), 1.03 (9H, s), 0.89(3H, d, J=6.7 Hz), 0.81(3H, d, J 6.8 Hz). 13 C-NMR; delta (CH3OD), 179.7, 176.6, 176.5, 172.0, 73.7, 56.9, 49.2, 39.5, 36.5, 28.3, 27.3, 24.5, 22.3, 21.2 and 21.1. LRMS; +ve ion 385 (M+H), −ve ion 383 (M−H).

EXAMPLE 19

2S,$N_1$-Dihydroxy-3R-isobutyl-$N_4$-[2-methyl-1S-(3-phenyl-[1,2,4]oxadiazol-5-yl)-propyl]-succinamide

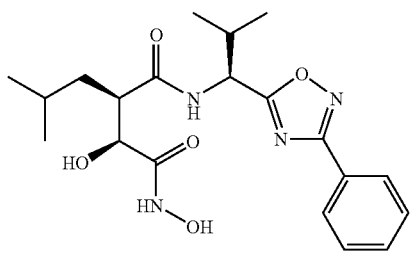

1H-NMR; delta(CH3OD), 8.05 (2H, m), 7.52 (3H, m), 5.14 (1H, d, J=7.2 Hz), 4.00 (1H, d, J=7.7 Hz), 2.91 (1H, m), 2.36 (1H, m), 1.63 (1H, m), 1.54 (1H, m), 1.16 (1H,m), 1.09 (3H, d, J=6.8 Hz), 1.00 (3H, d, J=6.8 Hz), 0.95(3H, d, J=6.3 Hz), 0.84(3H, d, J=6.3 Hz). 13 C-NMR; delta (CH3OD), 181.0, 176.8, 172.0, 169.9, 132.9, 130.5, 128.7, 128.4, 73.7, 54.3, 49.6, 39.5, 33.3, 27.2, 24.4, 22.5, 19.8 and 19.4. LRMS; +ve ion 427 (M+Na), −ve ion 403 (M−H).

The compounds of Examples 20-23 were prepared by the method of Example 2, by using the appropriate nitrile in Step C and/or the appropriate amino acid residue in Step A. The synthesis to the appropriate chiral succinate in Step E is detailed within WO 94/21625.

EXAMPLE 20

2S-Allyl-5-methyl-3R-[2-phenyl-1S-(3-phenyl-[1,2,4]oxadiazol-5-yl)-ethylcarbamoyl]-hexanohydroxamic acid

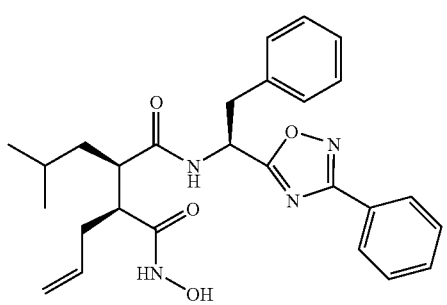

1H-NMR; delta (CH3OD), 9.13 (1H, d, J=8.26 Hz), 8.05 (2H, m), 7.55 (3H, m), 7.25 (5H, m), 5.66 (1H, m), 5.45 (1H, m), 4.90 (2H, m), 4.50 (1H,s) 3.51 (1H, dd, J=13.92, 4.84 Hz), 3.17 (1H, dd, J=13.92, 10.90 Hz), 2.50 (1H, m), 2.0 (2H, m), 1.50 (3H, m), 1.0 (3H, d, J=6.5 Hz), 0.96 (3H, d, J=6.6 Hz). 13C-NMR; delta (CH3OD), 181.0, 177.0, 172.7, 138.0, 136.5, 133., 130.8, 130.6, 130.5, 130.1, 128.7, 128.7, 117.7, 48.4, 48.3, 42.1, 39.5, 36.2, 27.1, 24.9 and 22.0.

EXAMPLE 21

2S-Allyl-5-methyl-3R-[2-phenyl-1S-(3-isopropyl-[1,2,4]oxadiazol-5-yl)-ethylcarbamoyl]-hexanohydroxamic acid

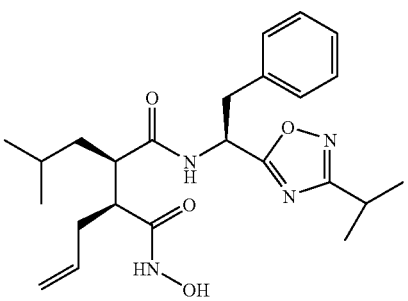

1H-NMR; delta (DMSO), 10.28 (1H, s), 8.64 (1H, d, J=6.2 Hz), 8.64 (1H, br s), 7.25 (5H, m), 5.45 (2H, m), 4.51 (1H, m), 4.30 (2H, m), 3.15 (1H, m), 2.85 (2H, m), 2.20 (1H, dt, J=10.6, 3.12 Hz), 1.70 (2H, m), 1.25 (6H, d, J=6.91 Hz), 0.70 (1H, m), 0.52 (3H, d, J=6.4 Hz), 0.48(3H, d, J=6.4 Hz). 13C-NMR; delta (MEOD), 179.0, 175.6, 175.5, 171.3, 136.6, 135.0, 129.2, 128.6, 127.3, 116.4, 48.7, 46.9, 40.6, 38.1, 34.8, 26.9, 25.6, 23.5, 20.7 and 19.9.

EXAMPLE 22

2S-Allyl-5-methyl-3R-[2-phenyl-1S-(3-methyl-[1,2,4]oxadiazol-5-yl)-ethylcarbamoyl]-hexanohydroxamic acid

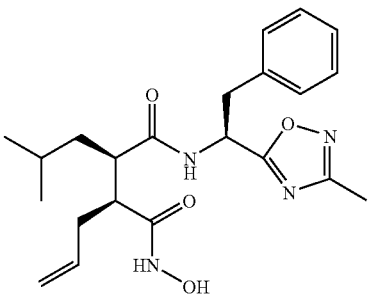

1H-NMR; delta (CH3OD), 8.98 (1H, d, J=8.41 Hz), 7.27 (5H, m), 5.51 (2H, m), 4.85 (2H, m), 3.41 (1H, dd, J=14.0, 5.0 Hz), 3.14 (1H, dd, J=14.0, 10.97 Hz), 2.47 (1H, dt, J=11.0, 3.25 Hz), 2.16 (3H, s), 2.00 (1H, dt, J=11.40, 3.30 Hz), 1.80 (1H, m), 1.15 (1H, m), 0.98 (3H, d, J=6.6 Hz), 0.92 (3H, d, J=6.6 Hz). 13C-NMR; delta (CH3OD), 172.62, 168.27, 133.59, 132.07, 126.34, 125.66, 124.28, 113.36, 45.19, 44.04, 43.95, 37.61, 35.15, 31.75, 22.72, 20.44, 17.59 and 7.36.

EXAMPLE 23

2S-Allyl-3R-[2,2-dimethyl-1S-(3-methyl-[1,2,4]oxadiazol-5-yl)-propylcarbamoyl]-5-methyl-hexanohydroxamic acid

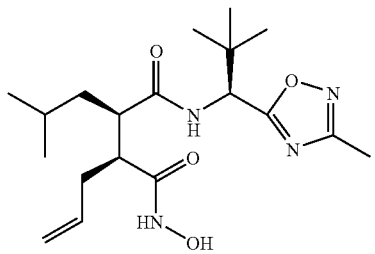

1H-NMR; delta (CH3OD), 8.81 (1H, d, J=8.59 Hz), 7.65 (1H, m), 5.70 (1H, m), 5.15 (1H, d, J=8.62 Hz), 4.95 (2H, m), 2.60 (1H, dt, J=11.10, 3.16 Hz), 2.39 (3H, s), 1.38 (1H, dt, J=13.10, 3.33 Hz), 1.31 (1H, m), 0.98 (1H, m), 0.98 (9H,s), 0.86(3H, d, J=6.6 Hz), 0.84(3H, d, J=6.6 Hz).

The compound of Example 24 was prepared by the method of Example 2. The synthesis to the appropriate chiral succinate in Step E is detailed within WO 95/19956

EXAMPLE 24

3R-[2,2-Dimethyl-1S-(3-phenyl-[1,2,4]oxadiazol-5-yl)-propylcarbamoyl]-5-methyl-hexanohydroxamic acid

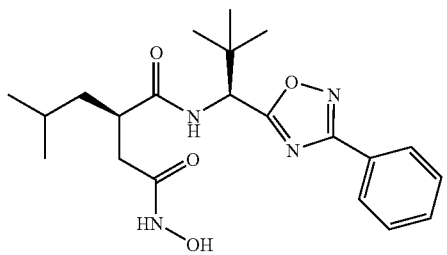

LRMS; +ve ion 403.5 (M+H), −ve ion 401.3 (M−H).

The compound of Example 25 was prepared by the method of Example 2, by using the appropriate nitrile in Step C and/or the appropriate amino acid residue in Step A. The synthesis to the appropriate chiral succinate in Step E is detailed within WO 97/02239.

EXAMPLE 25

2S-Methoxy-5-methyl-3R-[1S-(3-methyl-[1,2,4]oxadiazol-5-yl)-2-phenyl-ethylcarbamoyl]-hexanohydroxamic acid

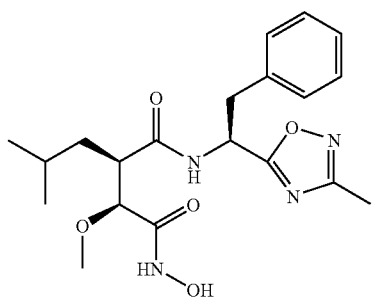

1H-NMR; delta (CH3OD), 7.14 (5H, m), 5.34 (1H, m), 3.38 (1H, d, J=9.68 Hz), 3.20 (2H, m), 3.02 (3H, s), 2.65 (1H, m), 2.22 (3H, s), 1.35 (2H, m), 0.90 (1H, m), 0.73 (3H, d, J=6.55 Hz), and 0.70 (3H, d, J=6.57 Hz).

The compounds of Example 26 and 27 were prepared by the method of Example 2. The synthesis to the appropriate chiral succinate in Step E is detailed within WO 92/13831 using methods analogous to those described in WO 95/32944.

EXAMPLE 26

3R-[2,2-Dimethyl-1S-(3-phenyl-[1,2,4]oxadiazol-5-yl)-propylcarbamoyl]-heptadecanoic acid

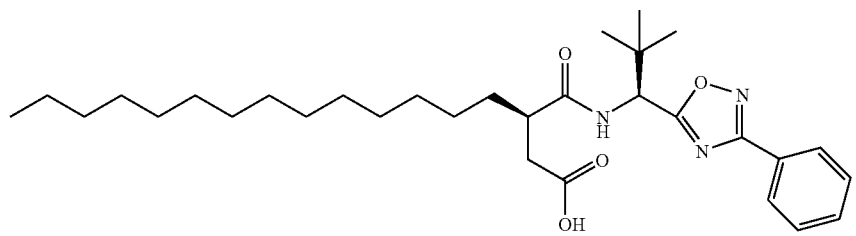

1H-NMR; delta(CH3OD), 8.05 (2H, m), 7.49 (3H, m), 5.22 (1H, s), 2.93 (1H, m), 2.65 (1H, dd, J=9.8, 16.7 Hz), 2.38 (1H, dd, J=4.6, 16.6 Hz), 1.52 (1H, m), 1.43 (1H, m), 1.26 (24H, m), 1.10 (9H, s) and 0.89 (3H, m). LRMS; +ve ion 528.4 (M+H).

EXAMPLE 27

3R-[2,2-Dimethyl-1S-(3-phenyl-[1,2,4]oxadiazol-5-yl)-propylcarbamoyl]-nonadecanoic acid

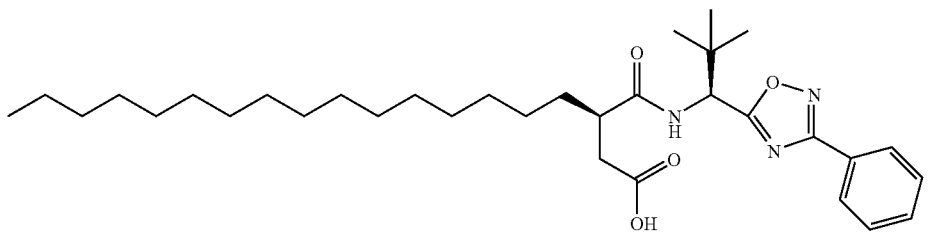

LRMS; +ve ion 556.2 (M+H).

The compound of Example 28 was prepared by the method of Example 1. The synthesis to the appropriate chiral succinate in Step H is detailed within WO 92/13831 using methods analogous to those described in WO 95/32944.

EXAMPLE 28

6-(4-Chloro-phenyl)-3R-[2,2-dimethyl-1S-(5-phenyl-[1,2,4]oxadiazol-3-yl)-propylcarbamoyl]-hexanoic acid

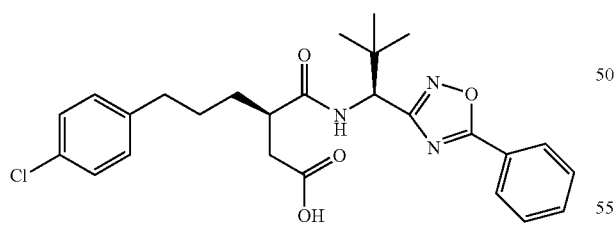

1H-NMR; delta(CH3OD), 8.07 (2H, m), 7.61 (3H, m), 6.93 (4H, m), 5.15 (1H, s), 2.94 (1H, m), 2.5 (4H, m), 1.5 (4H, m) and 1.07 (9H, s). 13 C-NMR; delta (CH3OD), 178.0, 177.1, 142.6, 134.6, 132.7, 131.0, 130.8, 129.5, 129.4, 125.7, 55.7, 43.8, 39.0, 36.3, 36.1, 34.1, 30.3 and 27.4. LRMS; +ve ion 506.2 (M+Na), −ve ion 482.4 (M−H).

Also prepared, the diastereomer 6-(4-Chloro-phenyl)-3R-[2,2-dimethyl-1R-(5-phenyl-[1,2,4]oxadiazol-3-yl)-propylcarbamoyl]-hexanoic acid

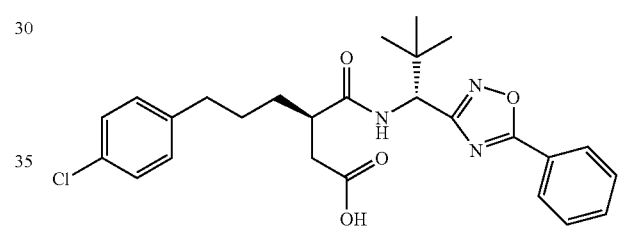

M+H =485, M+Na =507.2, M−H =482.6.

The compounds of Examples 29 and 30 were prepared by the method of Example 1.

EXAMPLE 29

3R-[2,2-Dimethyl-1S-(5-thiophen-2-yl-[1,2,4]oxadiazol-3-yl)-propylcarbamoyl]-2S-hydroxy-5-methyl-hexanoic acid

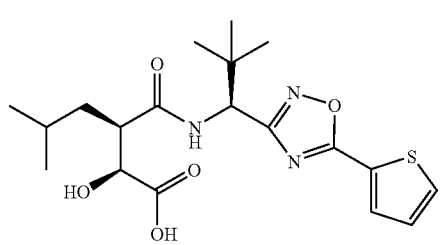

1H-NMR; delta (CH3OD), 7.95 (1H, m), 7.87 (1H, d, J=5.0 Hz), 7.28 (1H, m), 5.15 (1H, s), 4.18 (2H, d, J=6.4 Hz), 2.94 (1H, m), 1.68 (1H, m), 1.48 (1H, m), 1.31 (1H, m), 1.06 (9H, s), 0.88 (3H, d, J=6.4 Hz) and 0.82 (3H, d, J=6.5 Hz). LRMS; −ve ion 408.2 (M−H).

EXAMPLE 30

3R-[1S-(5-Furan-2-yl-[1,2,4]oxadiazol-3-yl)-2,2-dimethyl-propylcarbamoyl]-2S-hydroxy-5-methyl-hexanoic acid

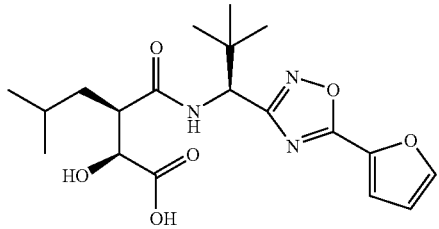

1H-NMR; delta (CH3OD), 7.88 (1H, s), 7.45 (1H, d, J=3.6 Hz), 6.74 (1H, m), 5.15 (1H, s), 4.18 (2H, d, J=6.4 Hz), 2.91 (1H, m), 1.65 (1H, m), 1.50 (1H, m), 1.31 (1H, m), 1.06 (9H, s), 0.88 (3H, d, J=6.4 Hz) and 0.82 (3H, d, J=6.5 Hz). LRMS; −ve ion 392.2 (M−H).

The compounds of Example 31 and 32 were prepared by the method of Example 2. The synthesis to the appropriate chiral succinate in Step E is detailed within WO 94/02446 using the appropriate cinnamyl bromide or cyclopentylmethyl iodide instead of the methallyl iodide as detailed in the aforementioned patent.

EXAMPLE 31

$N_4$-[2,2-Dimethyl-1S-(3-phenyl-[1,2,4]oxadiazol-5-yl)-propyl]-2S,$N_1$-dihydroxy-3R-(3-phenyl-allyl)-succinamide

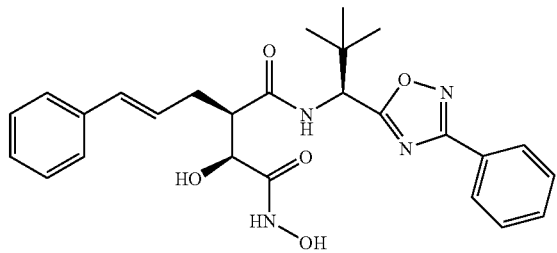

1H-NMR; delta(CH3OD), 7.95 (2H, d, J=7.2 Hz), 7.53 (1H, m), 7.48 (2H, m), 7.09 (2H, d, J=6.4 Hz), 6.91 (3H, m), 6.31 (1H, d, J=15.8 Hz), 6.04 (1H, m), 5.26 (1H, s), 4.14 (1H, d, J=7.6 Hz), 3.02 (1H, m), 2.46 (1H, m), 2.37 (1H, m), and 1.07 (9H, s). 13 C-NMR; delta (CH3OD), 179.8, 175.9, 172.0, 169.6, 138.8, 134.0, 132.8, 130.4, 129.7, 128.9, 128.4, 128.4, 127.3, 73.2, 56.5, 51.3, 36.8 and 34.0. LRMS; +ve ion 501.2 (M+Na), −ve ion 477.4 (M−H).

EXAMPLE 32

2R-Cyclopentylmethyl-3S,$N_4$-dihydroxy-$N_1$-[1S-(3-isopropyl-[1,2,4]oxadiazol-5-yl)-2,2-dimethyl-propyl]-succinamide

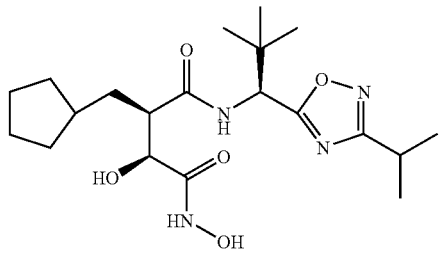

1H-NMR; delta(CH3OD), 5.13 (1H, s), 3.99 (1H, d, J=7.7 Hz), 3.06 (1H, m), 2.87 (1H, m), 1.83 (1H, m), 1.72 (1H, m), 1.63-1.39 (6H, bm), 1.31 (6H, d, J=6.9 Hz), 1.27 (1H, m), 1.03 (9H, s) and 1.02 (2H, m). 13 C-NMR; delta (CH3OD), 179.6, 176.6, 176.5, 172.0, 73.6, 56.8, 50.8, 39.6, 36.7, 36.5, 34.7, 33.6, 28.3, 27.2, 26.5 and 21.2. LRMS; +ve ion 411.2 (M+H), −ve ion 409.6 (M−H).

The compounds of Examples 33-35 were prepared by the method of Example 3 using the appropriate aryl bromide in Step B.

EXAMPLE 33

2R-[3-(3,5-Bis-trifluoromethyl-phenyl)-propyl]-$N_1$-[2,2-dimethyl-1S-(5-thiophen-2-yl-[1,2,4]oxadiazol-3-yl)-propyl]-3S,$N_4$-dihydroxy-succinamide

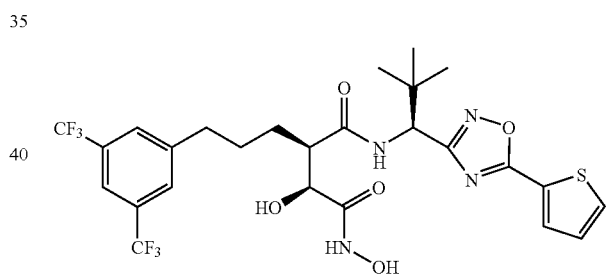

1H-NMR; delta(CH3OD), 8.38 (1H, d, J=9.4 Hz), 7.86 (1H, s), 7.75 (3H, bs), 7.4 (1H, d, J=3.5 Hz), 6.7 (1H, m), 5.12 (1H, d, J=9.4 Hz), 4.26 (1H, d, J=4.0 Hz), 2.8 (3H, bm), 1.8 (4H, bm) and 1.0 (9H, s).
LRMS; +ve ion 623.2 (M+H), −ve ion 621.0 (M−H).

EXAMPLE 34

2R-[3-(3,5-Bis-trifluoromethyl-phenyl)-propyl]-$N_1$-[1S-(5-furan-2-yl-[1,2,4]oxadiazol-3-yl)-2,2-dimethyl-propyl]-3S,$N_4$-dihydroxy-succinamide

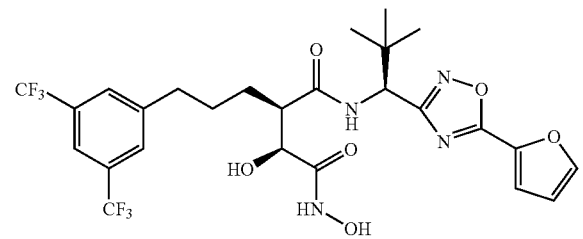

1H-NMR; delta(CH3OD), 8.38 (1H, d, J=9.4 Hz), 7.86 (1H, s), 7.75 (3H, bs), 7.4 (1H, d, J=3.5 Hz), 6.7 (1H, m), 5.12 (1H, d, J=9.4 Hz), 4.26 (1H, d, J=4.0 Hz), 2.8 (3H, bm), 1.8 (4H, bm) and 1.0 (9H, s). LRMS; +ve ion 629.4 (M+Na), −ve ion 605.4 (M−H).

EXAMPLE 35

2R-[3-(4-Ethoxy-phenyl)-propyl]-N$_1$-[1S-(5-furan-2-yl-[1,2,4]oxadiazol-3-yl)-2,2-dimethyl-propyl]-3S, N$_4$-dihydroxy-succinamide

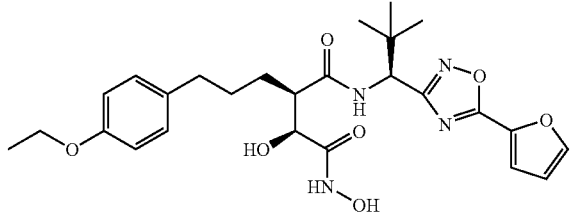

1H-NMR; delta(CH3OD), 7.86 (2H, m), 7.25 (1H, dd, J=3.8 Hz), 6.83 (2H, d, J=8.6 Hz), 6.54 (2H, d, J=8.6 Hz), 5.14 (1H, s), 4.03 (1H, d, J=7.6 Hz), 3.87 (2H, q, J=6.96, 14.0 Hz), 2.88 (1H, m), 2.45 (2H, bm), 1.53 (4H, bm), 1.33 (3H, t, J=7.0 Hz) and 1.06 (9H, s). LRMS; +ve ion 515.2 (M+H), −ve ion 513.2 (M−H).

The compound of Examples 36 was prepared by the method of Example 2. The synthesis to the appropriate chiral succinate in Step E is detailed within WO 01/10834.

EXAMPLE 36

3-Cyclopentyl-N-[2,2-dimethyl-1S-(3-phenyl-[1,2,4] oxadiazol-5-yl)-propyl]-2R-[(formyl-hydroxy-amino)-methyl]-propionamide

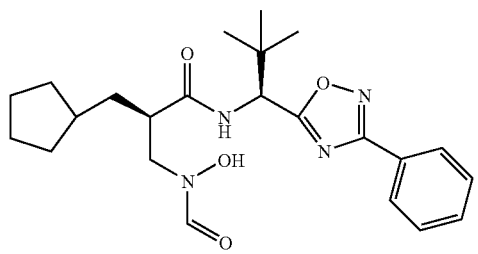

1H-NMR; delta(CH3OD), 8.26 (03H, s), 8.05 (2H, d, J=6.9 Hz), 7.84 (0.7H, s), 7.52 (3H, m), 5.20 (1H, m), 3.75 (1H, m), 3.63 (0.3H, dd, J=13.9, 5.5 Hz), 3.43 (0.7H, dd, J=14.2, 4.6 Hz), 3.18 (0.7H, m), 3.00 (0.3H, m), 1.92 (1H, m), 1.47 (8H, m), 1.10 (3H, s), 1.08 (6H, s) and 0.98 (2H, m). 13 C-NMR; delta (CH3OD) 179.9, 176.9, 176.6, 169.3, 163.8, 159.2, 132.5, 130.0, 129.6, 128.9, 128.3, 127.9, 56.8, 56.7, 53.9, 50.3, 44.8, 44.6, 39.1, 38.9, 37.9, 37.7, 35.9, 35.8, 34.1, 33.4, 33.3, 26.9, 26.1 and 25.9. LRMS; +ve ion 451 (M+Na), −ve ion 427 (M−H).

The compound of Example 37 was prepared by the method of Example 1. The synthesis to the appropriate chiral succinate in Step E is detailed within WO 01/10834.

EXAMPLE 37

3-Cyclopentyl-N-[2,2-dimethyl-1S-(5-phenyl-[1,2,4] oxadiazol-3-yl)-propyl]-2R-[(formyl-hydroxy-amino)-methyl]-propionamide

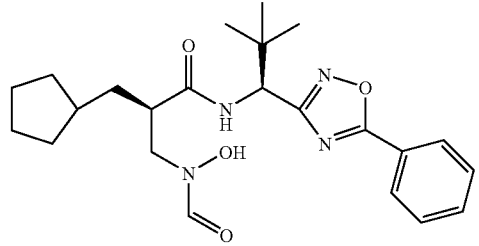

1H-NMR; delta(CH3OD), 8.49 (0.6H, d, J=8.7 Hz), 8.37 (0.4H, d, J=8.1 Hz), 8.28 (0.4H, s), 8.14 (2H, m), 7.85 (0.6H, s), 7.65 (1H, m), 7.59 (2H, m), 4.81 (1H, s), 3.79 (1H, m), 3.63 (0.4H, m), 3.43 (0.6H, m), 3.13 (0.6H, m), 2.97 (0.4H, m), 1.55 (9H, m), 1.08 (3H, s), 1.07 (6H, s) and 1.04 (2H, m). 13 C-NMR; delta (CH3OD), 176.6, 171.6, 164.2, 159.7, 134.6, 132.8, 130.8, 130.3, 129.4, 125.7, 69.5, 56.0, 54.3, 50.8, 45.4, 45.3, 40.6, 39.5, 38.3, 38.2, 35.9, 34.5, 33.8, 33.7, 32.0, 27.5, 26.4 and 26.3. LRMS; +ve ion 429 (M+H).

Biological Results

A. Enzyme Inhibition Assays

Compounds of the invention were tested to assess their activities as inhibitors of MMP9 and MMP12.

MMP9 Assay Protocol

Compounds were tested for inhibitory activity against 92 kDa gelatinase (MMP9) in an assay using a coumarin-labelled peptide substrate, (7-methoxycoumarin4-yl)acetyl-Pro-Leu-Gly-Leu-(3-[2,4-dinitrophenyl]-L-2,3-diaminopropionyl)-Ala-Arg-NH$_2$ (McaPLGLDpaAR) (Knight et al, FEBS Lett. 1992; 263-266).

Stock solutions were made up as follows:
Assay Buffer: 100 mM Tris-HCl pH 7.6 containing 100 mM NaCl, 10 mM CaCl$_2$, and 0.05% Brij 35
Substrate: 0.4 mM McaPLGLDpaAR (from Bachem) (0.437mg/ml) stock solution in 100%
DMSO (stored at −20° C.). Dilute to 8 µM in assay buffer.
Enzyme: Recombinant human 92 kDa gelatinase (MMP-9; APMA (4-aminophenyl
mercuric acetate)—activated if necessary) appropriately diluted in assay buffer.

Test Compounds were prepared initially as 10 mM compound solution in 100% DMSO, diluted to 1 mM in 100% DMSO, then serially diluted 3-fold in 100% DMSO across columns 1-10 of a 96-well microtitre plate Assay concentration range, 100 µM (column 1) to 5.1 nM (column 10)

The assay was performed in a total volume of 100 µl per well in 96-well microtitre plates. Activated enzyme (20 µl) was added to the wells followed by 20 µl of assay buffer. Appropriate concentrations of test compounds dissolved in 10 µl of DMSO were then added followed by 50 µl of McaPLGLDpaAR (8 µM, prepared by dilution of DMSO stock in assay buffer). For each assay ten concentrations of test compound were examined in duplicate. Control wells lack either enzyme or test compound. The reactions were incubated at 37° C. for 2 hours. The fluorescence at 405 nm was measured immediately with an SLT Fluostar fluorometer (SLT Labinstruments GmbH, Grödig, Austria) using 320 nm excitation, without stopping the reaction.

The effect of the test compound was determined from the dose response curve generated by the 10 duplicate concentrations of inhibitor. The $IC_{50}$ (the concentration of compound required to give a 50% decrease in enzyme activity) was obtained by fitting data to the equation, $Y=a+((b-a)/(1+(c/X)^d))$. (Y=inhibition achieved for a particular dose; X=the dose in nM; a=minimum y or zero % inhibition; b=maximum y or 100% inhibition; c=is the $IC_{50}$; d=is the slope). The result was rounded to one significant figure.

MMP12 Assay Protocol

Compounds were tested for inhibitory activity against metalloelastase (MMP12) in an assay using a coumarin-labelled peptide substrate, (7-methoxycoumarin4-yl)acetyl-Pro-Leu-Gly-Leu-(3-[2,4-dinitrophenyl]-L-2,3-diaminopropionyl)-Ala-Arg-NH$_2$ (McaPLGLDpaAR) (Knight et al, FEBS Lett. 1992; 263-266). The protocol for this assay was as described for the MMP9 assay above.

MMP1 Assay Protocol

Compounds were tested for inhibitory activity against collagenase (MMP1) in an assay using a coumarin-labelled peptide substrate, (7-methoxycoumarin4-yl)acetyl-Pro-Leu-Gly-Leu-(3-[2,4-dinitrophenyl]-L-2,3-diaminopropionyl)-Ala-Arg-NH$_2$ (McaPLGLDpaAR) (Knight et al, FEBS Lett. 1992; 263-266). The protocol for this assay was as described for the MMP9 assay above.

Results:

| Key to biological data | | | |
|---|---|---|---|
| Range | A | | <100 nM |
| | B | | 100-1000 nM |
| | C | | 1000-10,000 nM |
| | D | | >10,000 nM |

| Example Number | MMP9 IC50(nM) | MMP12 IC50(nM) | MMP1 IC50(nM) |
|---|---|---|---|
| 1 | B | A | B |
| 2 | B | A | B |
| 3 | A | A | D |
| 4 | B | A | B |
| 5 | B | A | B |
| 6 | C | A | B |
| 7 | C | B | C |
| 8 | B | A | B |
| 9 | C | A | B |
| 10 | C | A | C |
| 11 | C | A | C |
| 12 | B | A | B |
| 13 | B | A | B |
| 14 | C | A | C |
| 15 | B | A | B |
| 16 | B | A | B |
| 17 | C | A | B |
| 18 | B | A | B |
| 19 | B | A | B |
| 20 | A | A | B |
| 21 | A | A | B |
| 22 | Not tested | Not tested | A |
| 23 | A | A | B |
| 24 | C | A | C |
| 25 | B | A | B |
| 26 | D | D | Not tested |
| 27 | D | D | Not tested |
| 28 | Not tested | D | Not tested |
| 29 | C | B | C |
| 30 | D | C | D |
| 31 | D | B | D |
| 32 | A | A | A |
| 33 | D | B | D |
| 34 | D | D | D |
| 35 | A | A | D |

These results show that in general, the compounds tested were active as inhibitors of MMP12, with certain examples showing selective inhibition of both MMP-9 and 12 relative to MMP-1.

B. $CCl_4$-Induced Liver Fibrosis Model

Carbon tetrachloride ($CCl_4$) induces liver fibrosis when administered intraperitoneally (Bulbena O, Culat J, Bravo M L., Inflammation 1997 October; 21(5):475-88). Compounds of the invention can be evaluated for their ability to prevent the $CCl_4$-induced formation of fibrotic tissue.

Animals

Male Sprague-Dawley rats, 7 weeks old, weight approx. 300 g from Charles River/Iffa-Crédo, St-Germain/l'Arbresle, France.

Rats were acclimatised for 5 days before commencing experiments, in air-conditioned rooms, 2 animals per cage, Temperature: 22° C.±2, Relative humidity: 55% ±10 Light: 12 hour cycle (7 a.m.-7 p.m.), Cage: Makrolon® cage 42.5×26.6×15 on each fitted with a stainless steel cover-feed rack.

The study involved the following groups of 8 animals each, as indicated below.

Group 1: "Sham" animals received $CCl_4$ vehicle (i.p.) and once daily, the vehicle of test substance (s.c.)

Group 2: Positive control group received $CCl_4$ (i.p.), and once daily, the vehicle of the test substance (s.c.)

Group 3: Experimental group received $CCl_4$ (i.p.), and once daily, 2 mg/kg s.c. of the compound of Example 13.

Group 4: Experimental group received $CCl_4$ (i.p.), and once daily, 10 mg/kg s.c. of the compound of Example 13.

Group 5: Experimental group received $CCl_4$ (i.p.), and once daily, 20 mg/kg s.c. of the compound of Example 13.

Rats were labelled on their tails. The labels were checked and renewed, if necessary, after every $CCl_4$ injection.

Procedure $CCl_4$ (Prolabo) in olive oil was administered every 3 days for three weeks by intraperitoneal injection (0.25 ml $CCl_4$/kg body weight, diluted in oil 1:1 vol:vol for a total volume of 0.5 ml/kg). Animals were weighed daily. If body weight decreased by more than 10% of the initial weight, the animal was excluded from the study.

Vehicles and compound were used as follows:

$CCl_4$ was administered in olive oil (prolabo) at a 1:1 dilution;

The compound of Example 13 was suspended in 0.25% Tween-80 and 0.25% carboxymethylcellulose in sterile 0.9% NaCl. The solution was kept at 4° C. throughout the experiment and used each day to prepare the suspensions.

The compound of Example 13 was administered daily by subcutaneous (s.c.) injection at a volume of administration of 5 ml/kg. Groups 1 and 2 were dosed s.c. with 5 ml/kg of vehicle. Freshly prepared solutions were used on each day of the experiment. Administrations were carried out each day at the same time.

The treatment of groups of this study was started for each animal at the time of the first $CCl_4$ administration and was continued for 21 consecutive days. The last administration of test substances or vehicle was done 1 day before the sacrifice of the animals.

Results

Death was reported for 16 animals. Date and supposed cause are reported in Table 1.

Serum Enzyme Levels

Animals were killed 21 days following the first $CCl_4$ administration by isofurane inhalation. Blood was withdrawn individually at the time of sacrifice, i.e. one day after the last administration of test substance or vehicle. Blood was centrifuged at 4° C. Plasma was carefully collected and aliquoted in 3 fractions. Plasma aspartate amino transferase (ASAT) and alanine amino transferase (ALAT) levels were measured in order to assess liver necrosis. Increased ASAT and ALAT levels in serum are associated with liver impairment. Average ASAT and ALAT levels for control animals and those treated with the compound of Example 13 at three different dosages are shown in FIG. 1 (Y-axis is units of enzyme activity per liter blood, IU/L). Subcutaneous treatment with the compound of Example 13 clearly decreases ASAT and ALAT levels compared to animals treated with vehicle. This demonstrates that the compound of Example 13 has a protective effect on the liver.

Histological Evaluation of Liver Fibrosis

Liver fibrosis was evaluated by measuring the area of fibrosis in the liver using microchotomy. Results are reported as percentage area that was fibrotic.

The liver was removed, the three lobes were dissected and samples were removed and either fixed in 10% formaldehyde or frozen at −80° C.

Liver sections were embedded in paraffin blocks. Sectioning and staining with Sirius red was performed. Quantification of the fibrosis in liver was carried out on a minimum of 3 sections taken from different locations in the liver. The quantitative analysis was performed using an image analyser (Imstar) and the software Morphostar.

Average area percentages of fibrosis in the livers of animals in the different groups were calculated, and the results are shown in FIG. 2.

B. IL2-Induced Peritoneal Recruitment of Lymphocytes

Administration of IL2 intraperitoneally causes migration of lymphocytes into the intraperitoneal cavity. This is a model for the cellular migration that occurs during inflammation.

Compounds of the invention inhibit IL2-induced lymphocyte recruitment.

Protocol

C3H/HEN mice (Elevage Janvier, France) were intraperitoneally injected with IL2 (Serono Pharmaceutical Research Institute, 20 µg/kg, in saline).

Compounds of the invention were suspended in 0.5% carboxymethylcellulose (CMC)/0.25% tween-20 and were administered by sc or po route (10 ml/kg) 15 min prior to administration of IL2.

Twenty-four hours after administration of IL2, peritoneal white blood cells were collected by 3 successive lavages of the peritoneal cavity with 5 ml phosphate buffered saline (PBS)-1 mM EDTA (+4° C.). The suspension was centrifuged (1700 g×10 min at +4° C.). The resulting pellet was suspended in 1 ml PBS-1 mM EDTA.

Lymphocytes were identified and counted using a Beckman/Coulter counter.

Experimental Design

The animals were divided into 5 groups (6 mice each group):

Group 1: (baseline) received 0.5% CMC/0.25% tween-20 (vehicle of compound of the invention) and saline (vehicle of IL2);

Group 2: (control IL2) received 0.5% CMC/0.25% tween-20 and injection of IL2;

Group 3: Experimental group (Compound of the invention Dose 1) received a compound of the invention and injection of IL2;

Group 4: Experimental group (Compound of the invention Dose 2) received a compound of the invention and injection of IL2;

Group 5: Experimental group (Compound of the invention Dose 3) received a compound of the invention and injection of IL2;

Group 6: Reference group received reference compound dexamethasone and injection of IL2

Calculation

Inhibition of lymphocyte recruitment was calculated as follows:

$$\% \text{ inhibition} = \frac{1-(LyX-Ly1)}{(Ly2-Ly1)} \times 100\%$$

Where Ly 1=Number of lymphocytes in group 1 (E3/µl), Ly 2=Number of lymphocytes in group 2 (E3/µl), Ly X=Number of lymphocytes in group X (3-5) (E3/µl)

The dose of compound of the invention required to inhibit lymphocyte recruitment by 50% (ID50) was calculated using a curve-fitting routine. Results are listed in Table 1.

TABLE 1

$ID_{50}$ for inhibition of IL2-induced peritoneal recruitment of lymphocytes by compounds of the invention

| Example | Dose range or doses (mg/kg) | Route | $ID_{50}$ (mg/kg) |
|---|---|---|---|
| dexamethasone | 0.1-1 | Subcutaneous | 0.05 |
| Example 13 | 0.03, 0.3, 3, 30 | Subcutaneous | 0.1 |
| Example 13 | 0.3, 3, 30 | Oral | 1 |
| Example 5 | 0.3, 1, 3, 10, 30 | Subcutaneous | 1 |

The invention claimed is:

1. A compound formula (IA) or (IB)

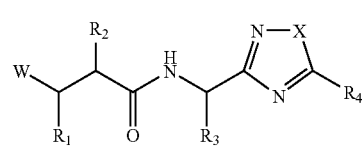

(IA)

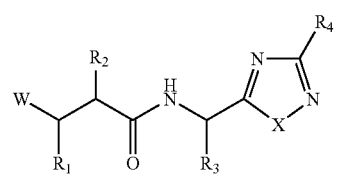

(IB)

wherein
W represents HO(C=O)—, HONH(C=O)— or H(C=O)N(OH)—;
X represents —O— or —S—;
$R_1$ represents
hydrogen;
—OH or —SH;
fluoro or chloro;
—$CF_3$;
($C_1$-$C_6$)alkyl;
($C_1$-$C_6$)alkoxy;
($C_2$-$C_6$)alkenyl; phenyl or substituted phenyl;
phenyl ($C_1$-$C_6$)alkyl or substituted phenyl($C_1$-$C_6$)alkyl;
phenyl ($C_2$-$C_6$)alkenyl or substituted phenyl($C_2$-$C_6$) alkenyl heterocyclyl or substituted heterocyclyl;
heterocyclyl($C_1$-$C_6$)alkyl or substituted heterocyclyl ($C_1$-$C_6$)alkyl;
a group $BSO_nA$- wherein n is 0, 1 or 2 and B is hydrogen or a ($C_1$-$C_6$)alkyl, phenyl, substituted phenyl, heterocyclyl, substituted heterocyclyl, ($C_1$-$C_6$)acyl, phenacyl or substituted phenacyl group, and A represents ($C_1$-$C_6$)alkylene;
—$NH_2$, ($C_1$-$C_6$)alkylamino or di($C_1$-$C_6$)alkylamino;
amino($C_1$-$C_6$)alkyl, ($C_1$-$C_6$)alkylamino($C_1$-$C_6$)alkyl, di($C_1$-$C_6$)alkylamino($C_1$-$C_6$)alkyl, hydroxy($C_1$-$C_6$) alkyl, mercapto($C_1$-$C_6$)alkyl or carboxy($C_1$-$C_6$)alkyl wherein the amino-, hydroxy-, mercapto- or carboxyl- group are optionally protected or the carboxyl-group amidated; or
a cycloalkyl, cycloalkenyl or non-aromatic heterocyclic ring containing up to 3 heteroatoms, any of which may be (i) substituted by one or more substituents selected from $C_1$-$C_6$ alkyl, $C_2$-$C_6$ alkenyl, halo, cyano (—CN), —$CO_2H$, —$CO_2R$, —$CONH_2$, —CONHR, —CON(R)$_2$, —OH, —OR, oxo-, —SH, —SR, —NH-COR, and —$NHCO_2R$ wherein R is $C_1$-$C_6$ alkyl or benzyl and/or (ii) fused to a cycloalkyl or heterocyclic ring;
$R_2$ represents a group $R_{10}$—$(X_1)_p$-$(ALK)_m$- wherein
$R_{10}$ represents hydrogen, or a $C_1$-$C_6$ alkyl, $C_2$-$C_6$ alkenyl, $C_2$-$C_6$ alkynyl, cycloalkyl, aryl, or heterocyclyl group, any of which may be unsubstituted or substituted by ($C_1$-$C_{12}$)alkyl, ($C_1$-$C_{12}$)alkoxy, hydroxy, mercapto, ($C_1$-$C_{12}$)alkylthio, amino, halo (including fluoro, chloro, bromo and iodo), trifluoromethyl, cyano, nitro, oxo, —COOH, —$CONH_2$, —$COOR^A$, —$NHCOR^A$, —$CONHR^A$, —$NHR^A$, —$NR^AR^B$, or —$CONR^AR^B$ wherein $R^A$ and $R^B$ are independently a ($C_1$-$C_{12}$)alkyl group and
ALK represents a straight or branched divalent $C_1$-$C_6$ alkylene, $C_2$-$C_6$ alkenylene, or $C_2$-$C_6$ alkynylene radical, and may be interrupted by one or more non-adjacent —NH—, —O— or —S-linkages,
$X_1$ represents —NH—, —O— or —S—, —$NR^c$ or —$NCOR^c$ wherein $R^c$ is a ($C_1$-$C_{12}$)alkyl group, and
m and p are independently 0 or 1;
$R^3$ is $C_1$-$C_6$ alkyl, phenyl, 2, 3-, or 4-pyridyl, 2- or 3-thienyl, 2-, 3-, or 4-hydroxyphenyl, 2-, 3-, or 4-methoxyphenyl, 2, 3-, or 4-pyridylmethyl, benzyl, 2, 3-, or 4-hydroxybenzyl, 2-, 3-, or 4-benzyloxybenzyl, 2-, 3-, or 4-$C_1$-$C_6$ alkoxybenzyl, or benzyloxy($C_1$-$C_6$ alkyl)-; or
the characterizing group of a natural α-amino acid, in which any functional group may be protected, any amino group may be acylated and any carboxyl group present may be amidated; or a group -[Alk]$_n R_6$ where Alk is a $C_1$-$C_6$)alkyl or $C_2$-$C_6$) alkenyl group optionally interrupted by one or more —O—, or —S— atoms or —N($R_7$) groups [where $R_7$ is a hydrogen atom or a ($C_1$-$C_6$)alkyl group], n is 0 or 1, and $R_6$ is an optionally substituted cycloalkyl or cycloalkenyl group; or
a benzyl group substituted in the phenyl ring by a group of formula —$OCH_2COR_8$ where $R_8$ is hydroxyl, amino, ($C_1$-$C_6$)alkoxy, phenyl($C_1$-$C_6$)alkoxy, ($C_1$-$C_6$) alkylamino, di(($C_1$-$C_6$)alkyl)amino, phenyl($C_1$-$C_6$) alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, seine, threonine, cysteine, methionine, asparagine, glutamine, lysine, histidine, arginine, glutamic acid, and aspartic acid; or
a heterocyclic($C_1$-$C_6$)alkyl group, either being unsubstituted or mono- or di-substituted in the heterocyclic ring with halo, nitro, carboxy, ($C_1$-$C_6$)alkoxy, cyano, ($C_1$-$C_6$)alkanoyl, trifluoromethyl ($C_1$-$C_6$)alkyl, hydroxy, formyl, amino, ($C_1$-$C_6$)alkylamino, di-($C_1$-$C_6$)alkylamino, mercapto, ($C_1$-$C_6$)alkylthio, hydroxy($C_1$-$C_6$) alkyl, mercapto($C_1C_6$)alkyl or $C_1$-$C_6$)alkylphenylmethyl; or
a group —$CR_aR_b$Rc in which;
each of $R_a$, $R_b$ and $R_c$ is independently hydrogen, ($C_1$-$C_6$)alkyl, ($C_2$-$C_6$)alkenyl, ($C_9$-$C_6$)alkynyl, phenyl($C_1$-$C_6$)alkyl, ($C_3$-$C_8$)cycloalkyl; or
$R_c$ is hydrogen and $R_a$ and $R_b$ are independently phenyl or heteroaryl such as pyridyl; or
$R_c$ is hydrogen, ($C_1$-$C_6$)alkyl, ($C_9$-$C_6$)alkenyl, ($C_2$-$C_6$) alkynyl, phenyl($C_1$-$C_6$)alkyl, or ($C_3$-$C_8$)cycloalkyl, and $R_a$ and $R_b$ together with the carbon atom to which they are attached form a 3 to 8 membered cycloalkyl or a 5- to 6-membered heterocyclic ring;
or $R_a$, $R_b$ and $R_c$ together with the carbon atom to which they are attached form a tricyclic ring (for example adamantyl); or
$R_a$ and $R_b$ are each independently ($C_1$-$C_6$)alkyl, ($C_2$-$C_6$) alkenyl, ($C_2$-$C_6$)alkynyl, phenyl($C_1$-$C_6$)alkyl, or a group as defined for $R_c$ below other than hydrogen, or $R_a$ and $R_b$ together with the carbon atom to which they are attached form a cycloalkyl or heterocyclic ring, and $R_c$ is hydrogen, —OH, —SH, halogen, —CN, —$CO_2H$, ($C_1$-$C_4$)perfluoroalkyl, —$CH_2OH$, —$CO_2$ ($C_1$-$C_6$)alkyl, —O($C_1$-$C_6$)alkyl, —O($C_2$-$C_6$)alkenyl, —S($C_1$-$C_6$)alkyl, —SO($C_1$-$C_6$)alkyl, —$SO_2$($C_1$-$C_6$) alkyl, —S($C_2$-$C_6$)alkenyl, —SO($C_2$-$C_6$)alkenyl, —$SO_2$ ($C_2$-$C_6$)alkenyl or a group -Q-W wherein Q represents a bond or —O—, —S—, —SO— or —$SO_2$— and W represents a phenyl, phenylalkyl, ($C_3$-$C_8$)cycloalkyl, ($C_3$-$C_8$)cycloalkylalkyl, ($C_4$-$C_8$)cycloalkenyl, ($C_4$-$C_8$) cycloalkenylalkyl, heteroaryl or heteroarylalkyl group, which group W may optionally be substituted by one or more substituents independently selected from, hydroxyl, halogen, —CN, —$CO_2H$, —$CO_2$($C_1$-$C_6$) alkyl, —$CONH_2$, —CONH($C_1$-$C_6$)alkyl, —CONH($C_1$-$C_6$ alkyl)$_2$, —CHO, —$CH_2OH$, ($C_1$-$C_4$)perfluoroalkyl, —O($C_1$-$C_6$)alkyl, —S($C_1$-$C_6$)alkyl, —SO($C_1$-$C_6$) alkyl, —$SO_2$($C_1$-$C_6$)alkyl,
—$NO_2$, —$NH_2$, —NH($C_1$-$C_6$)alkyl, —N(($C_1$-$C_6$)alkyl)$_2$, —NHCO($C_1$-$C_6$)alkyl, ($C_1$-$C_6$)alkyl, ($C_2$-$C_6$)alkenyl, ($C_1$-$C_6$)alkynyl, ($C_3$-$C_6$)cycloalkyl, ($C_4$-$C_8$)cycloalkenyl, phenyl or benzyl;

R₄ represents optionally substituted
- $C_1$-$C_6$ alkyl,
- $C_2$-$C_6$ alkenyl,
- $C_2$-$C_6$ alkynyl,
- $C_1$-$C_3$ perfluoroalkyl,
- cycloalkyl,
- cycloalkyl($C_1$-$C_6$ alkyl),
- cycloalkenyl,
- cycloalkenyl($C_1$-$C_6$ alkyl)-,
- phenyl,
- phenyl($C_1$-$C_6$ alkyl)-,
- naphthyl,
- non-aryl heterocyclyl,
- non-aryl heterocyclyl ($C_1$-$C_6$)alkyl-,
- heteroaryl; or
- heteroaryl($C_1$-$C_6$ alkyl)-;

or a pharmaceutically acceptable salt, hydrate or solvate thereof.

2. A compound as claimed in claim 1 wherein the compound has formula (IA).

3. A compound as claimed in claim 1 wherein the compound has formula (IB).

4. A compound as claimed in claim 1 wherein W is HONH(C=O)—.

5. A compound as claimed in claim 1 wherein X is —O—.

6. A compound as claimed in claim 1 wherein $R_1$ is hydrogen, hydroxy, fluoro, chloro, methyl, methoxy, trifluoromethyl, ethyl, n-propyl, allyl, phenylpropyl, cyclopropylmethyl, phenylprop-2-enyl, thienylsulphanylmethyl, thienylsulphinylmethyl, or thienylsulphonylmethyl; or $C_1$-$C_4$ alkyl, methyl, ethyl n-propyl or n-butyl, substituted by a phthalimido, 1,2-dimethyl-3,5-dioxo-1,2,4-triazolindin-4-yl, 3-methyl-2,5-dioxo-1-imidazolidinyl, 3,4,4-trimethyl-2,5-dioxo-1-imidazolidinyl, 2-methyl-3,5-dioxo-1,2,4-oxadiazol-4-yl, 3-methyl-2,4,5-trioxo-1-imidazolidinyl, 2,5-dioxo-3-phenyl-1-imidazolidinyl, 2-oxo-1-pyrrolidinyl, 2,5-dioxo-1-pyrrolidinyl or 2,6-dioxopiperidinyl, 5,5-dimethyl-2,4-dioxo-3-oxazolidinyl, hexahydro-1,3-dioxopyrazolo[1,2,a][1,2,4]-triazol-2-yl, or a naphthalimido (1,3-dihydro-1,3-dioxo-2H-benz[f]isoindol-2-yl), 1,3-dihydro-1-oxo-2H-benz[f]isoindol-2-yl, 1,3-dihydro-1,3-dioxo-2H-pyrrolo[3,4-b]quinolin-2-yl, or 2,3-dihydro-1,3-dioxo-1H-benz[d,e]isoquinolin-2-yl group; or cyclohexyl, cyclooctyl, cycloheptyl, cyclopentyl, cyclobutyl, cyclopropyl, tetrahydropyranyl or morpholinyl.

7. A compound as claimed in claim 1 wherein $R_1$ is hydrogen, hydroxy, $C_2$-$C_4$ alkenyl or $C_1$-$C_4$ alkoxy.

8. A compound as claimed in claim 1 wherein $R_1$ is hydrogen, hydroxy, fluoro, methoxy, cyclopentyl, n-propyl, or allyl.

9. A compound as claimed in claim 1 wherein $R_2$ is $C_1$-$C_{12}$ alkyl, $C_3$-$C_6$ alkenyl or $C_3$-$C_6$ alkynyl;
cycloalkyl($C_1$-$C_6$ alkyl)-;
phenyl($C_1$-$C_6$ alkyls, phenyl($C_3$-$C_6$ alkenyl)- or phenyl ($C_3$-$C_6$ alkynyl)- optionally substituted in the phenyl ring;
heteroaryl($C_1$-$C_6$ alkyl)-, heteroaryl($C_3$-$C_6$ alkenyl)- or heteroaryl($C_3$-$C_6$ alkynyl)- optionally substituted in the heteroaryl ring;
4-phenylphenyl($C_1$-$C_6$ alkyl), 4-phenylphenyl($C_3$-$C_6$ alkenyl)-, 4-phenylphenyl($C_3$-$C_6$ alkynyly, 4-heteroarylphenyl($C_1$-$C_6$ alkyl)-, 4-heteroarylphenyl($C_3$-$C_6$ alkenyl), 4-heteroarylphenyl($C_3$-$C_6$ alkynyl)-, optionally substituted in the terminal phenyl or heteroaryl ring;
or phenoxy($C_1$-$C_6$ alkyl)- or heteroaryloxy($C_1$-$C_6$ alkyl)- optionally substituted in the phenyl or heteroaryl ring.

10. A compound as claimed in claim 1 wherein $R_2$ is methyl, ethyl, n- or iso-propyl, n-, iso- or tert-butyl, n-phenyl, n-hexyl, n-heptyl, n-nonyl, n-decyl, prop-2-yn-1-yl, cyclohexylethyl, cyclopentylmethyl, 3-phenylprop-2-yn-1-yl, 3-(2-chlorophenyl)prop-2-yn-1-yl, benzyl phenylpropyl, 4-chlorophenylpropyl, 4-methylphenylpropyl, 4-methoxyphenylpropyl, phenoxybutyl, 3-(4-pyridylphenyl)propyl-, 3-(4-(4-pyridyl)phenyl)prop-2-yn-1-yl, 3-(4-phenylphenyl)propyl-, 3-(4-(phenyl)phenyl)prop-2-yn-1-yl or 3-[(4-chlorophenyl)phenyl]propyl-.

11. A compound as claimed in claim 1 wherein $R_2$ is $C_1$-$C_4$ alkyl, 3-8 membered cycloalkyl-$C_1$-$C_4$ alkyl- optionally containing 1-3 heteroatoms in the ring selected from N, O and S, or aryl-$C_1$-$C_4$ alkyl.

12. A compound as claimed in claim 1 wherein $R_2$ is benzyl, n-butyl, iso-butyl, n-hexyl, cyclopentylmethyl, 4-ethoxyphenylpropyl or phenylpropyl.

13. A compound as claimed in claim 1 wherein $R_3$ is benzyl, phenyl, cyclohexylmethyl, pyridin-3-ylmethyl, tert-butoxymethyl, iso-propyl, iso-butyl, sec-butyl, tert-butyl, 1-benzylthio-1-methylethyl, 1-methythio-1-methylethyl, or 1-mercapto-1-methylethyl.

14. A compound as claimed in claim 1 wherein $R_3$ is ($C_1$-$C_4$)alkyl or aryl- is ($C_1$-$C_4$)alkyl.

15. A compound as claimed in claim 1 wherein $R_3$ is benzyl, tert-butoxymethyl, iso-propyl, tert-butyl, or iso-butyl.

16. A compound as claimed in claim 1 wherein $R_4$ is optionally substituted ($C_1$-$C_6$)alkyl; ($C_3$-$C_8$)cycloalkyl; phenyl; monocyclic heterocyclic; or monocyclic heteroaryl.

17. A compound as claimed in claim 1 wherein $R_4$ is $C_1$-$C_4$ alkyl; heteroaryl; 3-8 membered cycloalkyl optionally containing 1-3 heteroatoms in the ring selected from N, O and S; or heteroaryl-$C_1$-$C_4$ alkyl.

18. A compound as claimed in claim 1 wherein $R_4$ is optionally substituted methyl, ethyl, n- or iso-propyl, prop-2-yl, tert-butyl, cyclopropyl, cyclopentyl; phenyl; morpholino; thienyl or furanyl.

19. A compound as claimed in claim 2 wherein $R_1$ is —OH; W is —C(=O)NHOH, X is —O— and $R_3$ is tert-butyl.

20. A compound as claimed in claim 2 wherein $R_1$ is —OH; W is —C(=O)NHOH, X is —O—, $R_3$ is tert-butyl, and $R_2$ is $C_1$-$C_{12}$ alkyl, or phenyl($C_1$-$C_{12}$ alkyl)- or heteroaryl($C_1$-$C_6$)alkyl)- which are optionally substituted in the phenyl or heteroaryl ring.

21. A compound as claimed in claim 2 wherein $R_1$ is —OH; W is —C(=O)NHOH, X is —O—, $R_3$ is tert-butyl, and $R_2$ is phenylpropyl- or ethoxyphenylpropyl.

22. A compound as claimed in claim 2 wherein $R_1$ is —OH; W is —C(=O)NHOH, X is —O—, $R_3$ is tert-butyl, and $R_4$ is branched $C_1$-$C_{12}$ alkyl, cycloalkyl, phenyl, heteroaryl, phenyl($C_1$-$C_6$ alkyl)- or heteroaryl($C_1$-$C_6$)alkyl)-.

23. A compound as claimed in claim 2 wherein $R_1$ is —OH; W is —C(=O)NHOH, X is —O—, $R_3$ is tert-butyl, $R_2$ is ethoxyphenylpropyl, and $R_4$ is phenyl or heteroaryl.

24. A compound as claimed in claim 3 wherein W is —C(=O)NHOH and X is —O—.

25. A compound as claimed in claim 3 wherein W is —C(=O)NHOH, X is —O—, and $R_3$ is tert-butyl.

26. A compound as claimed in claim 3 wherein W is —C(=O)NHOH, X is —O—, and $R_1$ is —OH, $C_1$-$C_6$ alkoxy, or $C_2$-$C_6$ alkenyl.

27. A compound as claimed in claim 3 wherein W is —C(=O)NHOH, X is —O—, $R_1$ is —OH, $C_1$-$C_6$ alkoxy, or $C_2$-$C_6$ alkenyl, $R_3$ is tert-butyl or benzyl and $R_4$ is isopropyl.

28. A compound selected from the group consisting of:

3R-[2,2-Dimethyl-1S-(5-phenyl-[1,2,4]oxadiazol-3-yl)-propylcarbamoyl]-2S-hydroxy-5-methyl-hexanohydroxamic acid;

3R-[2,2-dimethyl-1S-(5-phenyl-[1,2,4]oxadiazol-3-yl)-propylcarbamoyl]-2R-hydroxy-5-methyl-hexanohydroxamic acid;

3R-[2,2-Dimethyl-1S-(3-phenyl-[1,2,4]oxadiazol-5-yl)-propylcarbamoyl]-2S-hydroxy-5-methyl-hexanohydroxamic acid;

2R-[3-(4-Ethoxy-phenyl)-propyl]-N1-[1S-(5-thiophen-2-yl)-[1,2,4]oxadiazol-3-yl)-2,2-dimethyl-propyl]-3S,N4-dihydroxy-succinamide;

2S-Hydroxy-3R-[1S-(5-isopropyl-[1,2,4]oxadiazol-3-yl)-2,2-dimethyl-propylcarbamoyl]-5-methyl hexanohydroxamic acid;

2S-Hydroxy-3R-[1S-(5-furan-2-yl-[1,2,4]oxadiazol-3-yl)-2,2-dimethyl-propylcarbamoyl]-5-methyl hexanohydroxamic acid;

2S-Hydroxy-3R-[1S-(5-cyclopentylmethyl-[1,2,4]oxadiazol-3-yl)-2,2-dimethyl-propylcarbamoyl]-5-methyl hexanohydroxamic acid;

2S-Hydroxy-3R-[1S-(5-thiophen-2-ylmethyl-[1,2,4]oxadiazol-3-yl)-2,2-dimethyl-propylcarbamoyl]-5-methyl hexanohydroxamic acid;

2S-Hydroxy-3R-[1S-(5-ethyl-[1,2,4]oxadiazol-3-yl)-2,2-dimethyl-propylcarbamoyl]-5-methyl hexanohydroxamic acid;

2S-Hydroxy-3R-[1S-(5-cyclopentyl-[1,2,4]oxadiazol-3-yl)-2,2-dimethyl-propylcarbamoyl]-5-methyl hexanohydroxamic acid;

2S-Hydroxy-3R-[1S-(5-benzyl-[1,2,4]oxadiazol-3-yl)-2,2-dimethyl-propylcarbamoyl]-5-methyl hexanohydroxamic acid;

2S-Hydroxy-3R-[1S-(5-isobutyl-[1,2,4]oxadiazol-3-yl)-2,2-dimethyl-propylcarbamoyl]-5-methyl hexanohydroxamic acid;

2S-Hydroxy-3R-[1S-(5-tert-butyl-[1,2,4]oxadiazol-3-yl)-2,2-dimethyl-propylcarbamoyl]-5-methyl hexanohydroxamic acid;

3R-[1S-(5-thiophen-2-yl-[1,2,4]oxadiazol-3-yl)-2,2-dimethyl-propylcarbamoyl]-5-methyl hexanohydroxamic acid;

2S-Hydroxy-3R-[1S-(5-(2,2-dimethyl-propyl)-[1,2,4]oxadiazol-3-yl)-2,2-dimethyl-propylcarbamoyl]-5-methyl hexanohydroxamic acid;

2S-Hydroxy-3R-[1S-(5-p-tolyl-[1,2,4]oxadiazol-3-yl)-2,2-dimethyl-propylcarbamoyl]-5-methyl hexanohydroxamic acid;

2S-Hydroxy-3R-[1S-(5-cyclopropyl-[1,2,4]oxadiazol-3-yl)-2,2-dimethyl-propylcarbamoyl]-5-methyl hexanohydroxamic acid;

2S-Hydroxy-3R-[1S-(5-methyl-[1,2,4]oxadiazol-3-yl)-2,2-dimethyl-propylcarbamoyl]-5-methyl hexanohydroxamic acid;

2S-Hydroxy-3R-[1S-(3-isopropyl-[1,2,4]oxadiazol-3-yl)-2,2-dimethyl-propylcarbamoyl]-5-methyl hexanohydroxamic acid;

2S,N1-Dihydroxy-3R-isobutyl-N4-[2-methyl-1S-(3-phenyl-[1,2,4]oxadiazol-5-yl)-propyl]-succinamide;

2S-Allyl-5-methyl-3R-[2-phenyl-1S-(3-phenyl-[1,2,4]oxadiazol-5-yl)-ethylcarbamoyl]-hexanohydroxamic acid;

2S-Allyl-5-methyl-3R-[2-phenyl-1S-(3-isopropyl-[1,2,4]oxadiazol-5-yl)-ethylcarbamoyl]-hexanohydroxamic acid;

2S-Allyl-3R-[2,2-dimethyl-1S-(3-methyl-[1,2,4]oxadiazol-5-yl)-propylcarbamoyl]-5-methyl-hexanohydroxamic acid;

3R-[2,2-Dimethyl-1S-(3-phenyl-[1,2,4]oxadiazol-5-yl)-propylcarbamoyl]-5-methyl-hexanohydroxamic acid;

2S-Methoxy-5-methyl-3R-[1S-(3-methyl-[1,2,4]oxadiazol-5-yl)-2-phenyl-ethylcarbamoyl]-hexanohydroxamic acid;

3R-[2,2-Dimethyl-1S-(3-phenyl-[1,2,4]oxadiazol-5-yl)-propylcarbamoyl]-heptadecanoic acid;

3R-[2,2-Dimethyl-1S-(3-phenyl-[1,2,4]oxadiazol-5-yl)-propylcarbamoyl]-nonadecanoic acid;

6-(4-Chloro-phenyl)-3R-[2,2-dimethyl-1S-(5-phenyl-[1,2,4]oxadiazol-3-yl)-propylcarbamoyl]-hexanoic acid;

6-(4-Chloro-phenyl)-3R-[2,2-dimethyl-1R-(5-phenyl-[1,2,4]oxadiazol-3-yl)-propylcarbamoyl]-hexanoic acid;

3R-[2,2-Dimethyl-1S-(5-thiophen-2-yl-[1,2,4]oxadiazol-3-yl)-propylcarbamoyl]-2S-hydroxy-5-methyl-hexanoic acid;

3R-[1S-(5-Furan-2-yl-[1,2,4]oxadiazol-3-yl)-2,2-dimethyl-propylcarbamoyl]-2S-hydroxy-5-methyl-hexanoic acid;

2R-Cyclopentylmethyl-3S,N4-dihydroxy-N1-[1S-(3-isopropyl-[1,2,4]oxadiazol-5-yl)-2,2-dimethyl-propyl]-succinamide;

2R-[3-(3,5-Bis-trifluoromethyl-phenyl)-propyl]-N1-[2,2-dimethyl-1S-(5-thiophen-2-yl-[1,2,4]oxadiazol-3-yl)-propyl]-3S,N4-dihydroxy-succinamide;

2R-[3-(3,5-Bis-trifluoromethyl-phenyl)-propyl]-N1-[1S-(5-furan-2-yl-[1,2,4]oxadiazol-3-yl)-2,2-dimethyl-propyl]-3S,N4-dihydroxy-succinamide;

2R-[3-(4-Ethoxy-phenyl)-propyl]-N1-[1S-(5-furan-2-yl-[1,2,4]oxadiazol-3-yl)-2,2-dimethyl-propyl]-3S,N4-dihydroxy-succinamide;

3-Cyclopentyl-N-[2,2-dimethyl-1S-(3-phenyl-[1,2,4]oxadiazol-5-yl)-propyl]-2R-[(formyl-hydroxy-amino)-methyl]-propionamide;

3-Cyclopentyl-N-[2,2-dimethyl-1S-(5-phenyl-[1,2,4]oxadiazol-3-yl)-propyl]-2R-[(formyl-hydroxy-amino)-methyl]-propionamide;

and pharmaceutically acceptable salts, hydrates or solvates thereof.

29. A pharmaceutical or veterinary composition comprising a compound as claimed in claim 1.

30. A process for the preparation of a compound as claimed in claim 1 in which W is a hydroxamic acid group HONH(C=O), which process causing an acid of general formula (IIA) or (IIB)

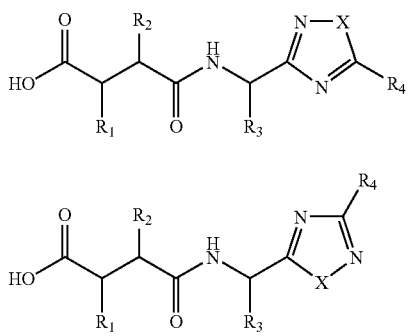

(IIA)

(IIB)

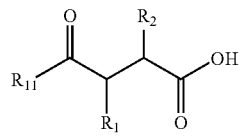

(III)

with an amine of formula (IVA) or (IVB)

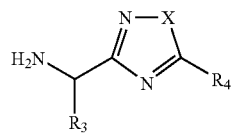

(IVA)

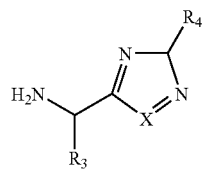

(IVB)

or an activated derivative thereof to react with hydroxylamine, O-protected hydroxylamine, or an N,O-diprotected hydroxylamine, or a salt thereof, X, $R_1$, $R_2$, $R_3$, and $R_4$ being as defined in claim 1 except that any substituents in $R_1$, $R_2$, $R_3$, and $R_4$ which are potentially reactive with hydroxylamine, O-protected hydroxylamine, the N,O-diprotected hydroxylamine or their salts are optionally themselves protected from such reaction, then removing any protecting groups from the resultant hydroxamic acid moiety and from any protected substituents in $R_1$, $R_2$, $R_3$, and $R_4$.

31. A process for the preparation of a compound as claimed in claim 1 wherein W is an N-formylhydroxylamino group H(C=O)NH(OH)— which process comprises N-formulation of the corresponding compound in which W is —NH(OP) wherein P is an O-protecting group, then removing the O-protecting group P.

32. A process for the preparation of a compound as claimed in claim 1 wherein W is a carboxylic acid group —COON, which process comprises: coupling an acid of formula (III) or an activated derivative thereof wherein X, $R_1$ $R_2$, $R_3$, and $R_4$ are as defined in claim 1 except that any substituents in $R_1$, $R_2$, $R_3$, and $R_4$ which are potentially reactive in the coupling reaction may themselves be protected from such reaction, and $R_{11}$ represents a hydroxy protecting group, and subsequently removing the protecting group $R_{11}$ and any protecting groups from $R_1$ $R_2$, $R_3$, and $R_4$.

33. 2S-Hydroxy-3R-[1S-(5-thiophen-2-yl-[1,2,4]oxadiazol-3-yl)-2,2-dimethyl-propylcarbamoyl]-5-methyl hexanohydroxamic acid and pharmaceutically acceptable salts, hydrates or solvates thereof.

* * * * *